(12) United States Patent
Strauss et al.

(10) Patent No.: US 9,289,215 B2
(45) Date of Patent: Mar. 22, 2016

(54) IMPLANT INCLUDING A COIL AND A STRETCH-RESISTANT MEMBER

(71) Applicant: Covidien LP, Mansfield, MA (US)

(72) Inventors: Brian Michael Strauss, Trabuco Canyon, CA (US); Todd Jeffrey Hewitt, Laguna Niguel, CA (US); Ramon Torres Carillo, Santa Ana, CA (US); Khoa Dang Vu, Santa Ana, CA (US); William Robert Patterson, Irvine, CA (US); Stacy Leon Faught, Aliso Viejo, CA (US); Lawrason Charles Wilbur, Lake Forest, CA (US); Scott William Brennan, Laguna Beach, CA (US); Vince Divino, Mission Viejo, CA (US)

(73) Assignee: Covidien LP, Mansfield, MA (US)

( * ) Notice: Subject to any disclaimer, the term of this patent is extended or adjusted under 35 U.S.C. 154(b) by 513 days.

(21) Appl. No.: 13/685,754

(22) Filed: Nov. 27, 2012

(65) Prior Publication Data
US 2013/0331883 A1    Dec. 12, 2013

Related U.S. Application Data

(63) Continuation of application No. 12/038,730, filed on Feb. 27, 2008, now Pat. No. 8,328,860.

(60) Provisional application No. 60/894,589, filed on Mar. 13, 2007, provisional application No. 60/894,858, filed on Mar. 14, 2007.

(51) Int. Cl.
*A61M 29/00* (2006.01)
*A61B 17/12* (2006.01)
(Continued)

(52) U.S. Cl.
CPC ....... *A61B 17/12113* (2013.01); *A61B 17/1215* (2013.01); *A61B 17/1219* (2013.01); *A61B 17/12022* (2013.01); *A61B 17/12145* (2013.01);
(Continued)

(58) Field of Classification Search
CPC .... A61B 17/12022; A61B 17/1214–17/12154; A61B 2017/12054–2017/21095
USPC ........... 606/108, 200; 623/1.11; 128/831, 843
See application file for complete search history.

(56) References Cited

U.S. PATENT DOCUMENTS

| 3,174,851 | A | 3/1965 | Buehler et al. |
| 3,334,629 | A | 8/1967 | Colm |

(Continued)

FOREIGN PATENT DOCUMENTS

| CN | 1668250 A | 9/2005 |
| DE | 4445715 | 6/1996 |

(Continued)

OTHER PUBLICATIONS

U.S. Appl. No. 13/308,476, filed Nov. 30, 2011.
(Continued)

*Primary Examiner* — Katherine Rodjom
*Assistant Examiner* — Jonathan Hollm
(74) *Attorney, Agent, or Firm* — Elizabeth A. O'Brien, Esq.

(57) ABSTRACT

This invention is directed to implantable coils and, more particularly, to a coil implant having a stretch-resistant member internal to the coil. The implant of the invention is able to freely articulate and torque prior to delivery. Once delivered, the implant is no longer stretch resistant and is therefore able to substantially conform to the vascular site.

22 Claims, 8 Drawing Sheets

(51) Int. Cl.
*A61B 17/00* (2006.01)
*A61B 19/00* (2006.01)

(52) U.S. Cl.
CPC . *A61B 17/12154* (2013.01); *A61B 2017/00004* (2013.01); *A61B 2017/12054* (2013.01); *A61B 2017/12059* (2013.01); *A61B 2017/12063* (2013.01); *A61B 2017/12068* (2013.01); *A61B 2017/12081* (2013.01); *A61B 2019/481* (2013.01)

(56) References Cited

U.S. PATENT DOCUMENTS

| | | |
|---|---|---|
| 3,753,700 A | 8/1973 | Harrison et al. |
| 3,834,394 A | 9/1974 | Hunter et al. |
| 4,085,757 A | 4/1978 | Pevsner |
| 4,282,875 A | 8/1981 | Serbinenko et al. |
| 4,311,146 A | 1/1982 | Wonder |
| 4,327,734 A | 5/1982 | White, Jr. |
| 4,341,218 A | 7/1982 | U |
| 4,346,712 A | 8/1982 | Handa et al. |
| 4,364,392 A | 12/1982 | Strother et al. |
| 4,402,319 A | 9/1983 | Handa et al. |
| 4,441,495 A | 4/1984 | Hicswa |
| 4,494,531 A | 1/1985 | Gianturco |
| 4,517,979 A | 5/1985 | Pecenka |
| 4,545,367 A | 10/1985 | Tucci |
| 4,638,803 A | 1/1987 | Rand |
| 4,677,191 A | 6/1987 | Tanaka et al. |
| 4,735,201 A | 4/1988 | O'Reilly |
| 4,781,177 A | 11/1988 | Lebigot |
| 4,787,899 A | 11/1988 | Lazarus |
| 4,819,637 A | 4/1989 | Dormandy, Jr. et al. |
| 4,832,055 A | 5/1989 | Palestrant |
| 4,944,746 A | 7/1990 | Iwata et al. |
| 4,957,501 A | 9/1990 | Lahille et al. |
| 4,990,155 A | 2/1991 | Wilkoff |
| 4,994,069 A | 2/1991 | Ritchart et al. |
| 5,002,556 A | 3/1991 | Ishida et al. |
| 5,026,377 A | 6/1991 | Burton et al. |
| 5,035,706 A | 7/1991 | Giantureo et al. |
| 5,037,427 A | 8/1991 | Harada et al. |
| 5,062,829 A | 11/1991 | Pryor et al. |
| 5,104,399 A | 4/1992 | Lazarus |
| 5,108,407 A | 4/1992 | Geremia et al. |
| 5,109,867 A | 5/1992 | Twyford, Jr. |
| 5,122,136 A | 6/1992 | Guglielmi et al. |
| 5,133,731 A | 7/1992 | Butler et al. |
| 5,133,732 A | 7/1992 | Wiktor |
| 5,147,370 A | 9/1992 | McNamara et al. |
| 5,167,624 A | 12/1992 | Butler et al. |
| 5,181,921 A | 1/1993 | Makita et al. |
| 5,192,301 A | 3/1993 | Kamiya et al. |
| 5,211,658 A | 5/1993 | Clouse |
| 5,217,484 A | 6/1993 | Marks |
| 5,222,970 A | 6/1993 | Reeves |
| 5,224,953 A | 7/1993 | Morgentaler |
| 5,226,911 A | 7/1993 | Chee et al. |
| 5,234,437 A | 8/1993 | Sepetka |
| 5,250,071 A | 10/1993 | Palermo |
| 5,256,146 A | 10/1993 | Ensminger et al. |
| 5,261,916 A | 11/1993 | Engelson |
| 5,263,964 A | 11/1993 | Purdy |
| 5,282,806 A | 2/1994 | Haber et al. |
| 5,304,194 A | 4/1994 | Chee et al. |
| 5,304,195 A | 4/1994 | Twyford, Jr. et al. |
| 5,312,415 A | 5/1994 | Palermo |
| 5,314,472 A | 5/1994 | Fontaine |
| 5,334,210 A | 8/1994 | Gianturco |
| 5,350,397 A | 9/1994 | Palermo et al. |
| 5,354,295 A | 10/1994 | Guglielmi et al. |
| 5,368,592 A | 11/1994 | Stern et al. |
| 5,382,259 A | 1/1995 | Phelps et al. |
| 5,382,260 A | 1/1995 | Dormandy, Jr. et al. |
| 5,382,261 A | 1/1995 | Palmaz |
| 5,397,345 A | 3/1995 | Lazarus |
| 5,417,708 A | 5/1995 | Hall et al. |
| 5,423,829 A | 6/1995 | Pham et al. |
| 5,423,849 A | 6/1995 | Engelson et al. |
| 5,443,454 A | 8/1995 | Tanabe et al. |
| 5,443,478 A | 8/1995 | Purdy |
| 5,456,693 A | 10/1995 | Conston et al. |
| 5,476,472 A | 12/1995 | Dormandy, Jr. et al. |
| 5,480,382 A | 1/1996 | Hammerslag et al. |
| 5,485,496 A | 1/1996 | Lee et al. |
| 5,498,227 A | 3/1996 | Mawad |
| 5,499,985 A | 3/1996 | Hein et al. |
| 5,507,769 A | 4/1996 | Marin et al. |
| 5,522,822 A | 6/1996 | Phelps et al. |
| 5,522,836 A | 6/1996 | Palermo |
| 5,527,338 A | 6/1996 | Purdy |
| 5,536,274 A | 7/1996 | Neuss |
| 5,540,680 A | 7/1996 | Guglielmi et al. |
| 5,549,624 A | 8/1996 | Mirigian et al. |
| 5,562,698 A | 10/1996 | Parker |
| 5,569,245 A | 10/1996 | Guglielmi et al. |
| 5,573,520 A | 11/1996 | Schwartz et al. |
| 5,578,074 A | 11/1996 | Mirigian |
| 5,582,619 A | 12/1996 | Ken |
| 5,601,600 A | 2/1997 | Ton |
| 5,624,449 A | 4/1997 | Pham et al. |
| 5,624,461 A | 4/1997 | Mariant |
| 5,626,599 A | 5/1997 | Bourne et al. |
| 5,634,928 A | 6/1997 | Fischell et al. |
| 5,639,277 A | 6/1997 | Mariant et al. |
| 5,643,254 A | 7/1997 | Scheldrup et al. |
| 5,645,558 A | 7/1997 | Horton |
| 5,645,564 A | 7/1997 | Northrup et al. |
| 5,649,949 A | 7/1997 | Wallace et al. |
| 5,658,308 A | 8/1997 | Snyder |
| 5,662,700 A | 9/1997 | Lazarus |
| 5,669,905 A | 9/1997 | Scheldrup et al. |
| 5,669,931 A | 9/1997 | Kupiecki et al. |
| 5,690,666 A | 11/1997 | Berenstein et al. |
| 5,690,667 A | 11/1997 | Gia |
| 5,690,671 A | 11/1997 | McGurk et al. |
| 5,693,067 A | 12/1997 | Purdy |
| 5,695,517 A | 12/1997 | Marin et al. |
| 5,700,258 A | 12/1997 | Mirigian et al. |
| 5,702,361 A | 12/1997 | Evans et al. |
| 5,718,711 A | 2/1998 | Berenstein et al. |
| 5,725,534 A | 3/1998 | Rasmussen |
| 5,725,546 A | 3/1998 | Samson |
| 5,725,552 A | 3/1998 | Kotula et al. |
| 5,733,329 A | 3/1998 | Wallace et al. |
| 5,743,905 A | 4/1998 | Eder et al. |
| 5,746,734 A | 5/1998 | Dormandy, Jr. et al. |
| 5,746,769 A | 5/1998 | Ton et al. |
| 5,749,891 A | 5/1998 | Ken et al. |
| 5,749,894 A | 5/1998 | Engelson |
| 5,749,918 A | 5/1998 | Hogendijk et al. |
| 5,759,161 A | 6/1998 | Ogawa et al. |
| 5,766,219 A | 6/1998 | Horton |
| 5,797,953 A | 8/1998 | Tekulve |
| 5,800,426 A | 9/1998 | Taki et al. |
| 5,800,453 A | 9/1998 | Gia |
| 5,800,455 A | 9/1998 | Palermo et al. |
| 5,814,062 A | 9/1998 | Sepetka et al. |
| 5,830,230 A | 11/1998 | Berryman et al. |
| 5,833,705 A | 11/1998 | Ken et al. |
| 5,843,118 A | 12/1998 | Sepetka et al. |
| 5,846,210 A | 12/1998 | Ogawa et al. |
| 5,851,206 A | 12/1998 | Guglielmi et al. |
| 5,853,418 A | 12/1998 | Ken et al. |
| 5,855,578 A | 1/1999 | Guglielmi et al. |
| 5,891,058 A | 4/1999 | Taki et al. |
| 5,891,128 A | 4/1999 | Gia et al. |
| 5,891,130 A | 4/1999 | Palermo et al. |
| 5,891,155 A | 4/1999 | Irie |
| 5,891,192 A | 4/1999 | Murayama et al. |
| 5,895,385 A | 4/1999 | Guglielmi et al. |
| 5,895,391 A | 4/1999 | Farnholtz |
| 5,895,410 A | 4/1999 | Forber et al. |
| 5,895,411 A | 4/1999 | Irie |

(56) References Cited

U.S. PATENT DOCUMENTS

| | | |
|---|---|---|
| 5,911,731 A | 6/1999 | Pham et al. |
| 5,911,737 A | 6/1999 | Lee et al. |
| 5,916,235 A | 6/1999 | Guglielmi |
| 5,919,187 A | 7/1999 | Guglielmi et al. |
| 5,925,037 A | 7/1999 | Guglielmi et al. |
| 5,925,059 A | 7/1999 | Palermo et al. |
| 5,925,060 A | 7/1999 | Forber |
| 5,925,062 A | 7/1999 | Purdy |
| 5,928,226 A | 7/1999 | Guglielmi et al. |
| 5,935,145 A | 8/1999 | Villar et al. |
| 5,935,148 A | 8/1999 | Villar et al. |
| 5,941,249 A | 8/1999 | Maynard |
| 5,941,888 A | 8/1999 | Wallace et al. |
| 5,944,714 A | 8/1999 | Guglielmi et al. |
| 5,944,733 A | 8/1999 | Engelson |
| 5,947,962 A | 9/1999 | Guglielmi et al. |
| 5,947,963 A | 9/1999 | Guglielmi |
| 5,957,948 A | 9/1999 | Mariant |
| 5,964,797 A | 10/1999 | Ho |
| 5,972,019 A | 10/1999 | Engelson et al. |
| 5,976,126 A | 11/1999 | Guglielmi |
| 5,976,131 A | 11/1999 | Guglielmi et al. |
| 5,976,152 A | 11/1999 | Regan et al. |
| 5,976,162 A | 11/1999 | Doan et al. |
| 5,980,514 A | 11/1999 | Kupiecki et al. |
| 5,980,550 A | 11/1999 | Eder et al. |
| 5,980,554 A | 11/1999 | Lenker et al. |
| 5,984,929 A | 11/1999 | Bashiri et al. |
| 5,984,944 A | 11/1999 | Forber |
| 5,989,242 A | 11/1999 | Saadat et al. |
| 6,001,092 A | 12/1999 | Mirigian et al. |
| 6,004,338 A | 12/1999 | Ken et al. |
| 6,010,498 A | 1/2000 | Guglielmi |
| 6,013,084 A | 1/2000 | Ken et al. |
| 6,015,424 A | 1/2000 | Rosenbluth et al. |
| 6,017,364 A | 1/2000 | Lazarus |
| 6,017,977 A | 1/2000 | Evans et al. |
| 6,019,757 A | 2/2000 | Scheldrup |
| 6,022,369 A | 2/2000 | Jacobsen et al. |
| 6,024,754 A | 2/2000 | Engelson |
| 6,024,765 A | 2/2000 | Wallace et al. |
| 6,030,413 A | 2/2000 | Lazarus |
| 6,033,423 A | 3/2000 | Ken et al. |
| 6,039,749 A | 3/2000 | Marin et al. |
| 6,056,770 A | 5/2000 | Epstein et al. |
| 6,059,779 A | 5/2000 | Mills |
| 6,059,815 A | 5/2000 | Lee et al. |
| 6,063,070 A | 5/2000 | Eder |
| 6,063,100 A | 5/2000 | Diaz et al. |
| 6,063,104 A | 5/2000 | Villar et al. |
| 6,066,133 A | 5/2000 | Guglielmi et al. |
| 6,066,149 A | 5/2000 | Samson et al. |
| 6,068,644 A | 5/2000 | Lulo et al. |
| 6,074,407 A | 6/2000 | Levine et al. |
| 6,077,260 A | 6/2000 | Wheelock et al. |
| D427,680 S | 7/2000 | Mariant et al. |
| 6,083,220 A | 7/2000 | Guglielmi et al. |
| 6,086,577 A | 7/2000 | Ken et al. |
| 6,090,125 A | 7/2000 | Horton |
| 6,093,199 A | 7/2000 | Brown et al. |
| 6,096,034 A | 8/2000 | Kupiecki et al. |
| 6,096,546 A | 8/2000 | Raskin |
| 6,102,917 A | 8/2000 | Maitland et al. |
| 6,102,932 A | 8/2000 | Kurz |
| 6,102,933 A | 8/2000 | Lee et al. |
| 6,113,622 A | 9/2000 | Hieshima |
| 6,117,142 A | 9/2000 | Goodson et al. |
| 6,123,714 A | 9/2000 | Gia et al. |
| 6,126,672 A | 10/2000 | Berryman et al. |
| 6,136,015 A | 10/2000 | Kurz et al. |
| 6,143,007 A | 11/2000 | Mariant et al. |
| 6,146,373 A | 11/2000 | Cragg et al. |
| 6,149,664 A | 11/2000 | Kurz |
| 6,149,681 A | 11/2000 | Houser et al. |
| 6,156,061 A | 12/2000 | Wallace et al. |
| 6,159,165 A | 12/2000 | Ferrera et al. |
| 6,159,206 A | 12/2000 | Ogawa |
| 6,165,178 A | 12/2000 | Bashiri et al. |
| 6,165,193 A | 12/2000 | Greene, Jr. et al. |
| 6,165,198 A | 12/2000 | McGurk et al. |
| 6,168,570 B1 | 1/2001 | Ferrera |
| 6,168,592 B1 | 1/2001 | Kupiecki et al. |
| 6,168,610 B1 | 1/2001 | Marin et al. |
| 6,168,615 B1 | 1/2001 | Ken et al. |
| 6,168,622 B1 | 1/2001 | Mazzocchi |
| 6,171,326 B1 | 1/2001 | Ferrera et al. |
| 6,183,491 B1 | 2/2001 | Lulo |
| 6,183,495 B1 | 2/2001 | Lenker et al. |
| 6,187,024 B1 | 2/2001 | Boock et al. |
| 6,187,027 B1 | 2/2001 | Mariant et al. |
| 6,190,373 B1 | 2/2001 | Palermo et al. |
| 6,193,708 B1 | 2/2001 | Ken et al. |
| 6,193,728 B1 | 2/2001 | Ken et al. |
| RE37,117 E | 3/2001 | Palermo |
| 6,202,261 B1 | 3/2001 | Moore et al. |
| 6,203,547 B1 | 3/2001 | Nguyen et al. |
| 6,221,066 B1 | 4/2001 | Ferrera et al. |
| 6,221,086 B1 | 4/2001 | Forber |
| 6,224,610 B1 | 5/2001 | Ferrera |
| 6,231,573 B1 | 5/2001 | Amor et al. |
| 6,231,586 B1 | 5/2001 | Mariant |
| 6,231,590 B1 | 5/2001 | Slaikeu et al. |
| 6,231,597 B1 | 5/2001 | Deem et al. |
| 6,238,403 B1 | 5/2001 | Greene, Jr. et al. |
| 6,238,415 B1 | 5/2001 | Sepetka et al. |
| 6,241,691 B1 | 6/2001 | Ferrera et al. |
| 6,254,592 B1 | 7/2001 | Samson et al. |
| 6,270,495 B1 | 8/2001 | Palermo |
| 6,277,125 B1 | 8/2001 | Barry et al. |
| 6,277,126 B1 | 8/2001 | Barry et al. |
| 6,280,457 B1 | 8/2001 | Wallace et al. |
| 6,281,263 B1 | 8/2001 | Evans et al. |
| 6,287,315 B1 | 9/2001 | Wijeratne et al. |
| 6,287,318 B1 | 9/2001 | Villar et al. |
| 6,293,960 B1 | 9/2001 | Ken |
| 6,296,622 B1 | 10/2001 | Kurz et al. |
| 6,299,619 B1 | 10/2001 | Greene, Jr. et al. |
| 6,299,627 B1 | 10/2001 | Eder et al. |
| 6,306,153 B1 | 10/2001 | Kurz et al. |
| 6,312,405 B1 | 11/2001 | Meyer et al. |
| 6,312,421 B1 | 11/2001 | Boock |
| 6,315,709 B1 | 11/2001 | Garibaldi et al. |
| 6,319,267 B1 | 11/2001 | Kurz |
| 6,322,576 B1 | 11/2001 | Wallace et al. |
| 6,331,184 B1 | 12/2001 | Abrams |
| 6,335,384 B1 | 1/2002 | Evans et al. |
| 6,344,041 B1 | 2/2002 | Kupiecki et al. |
| 6,344,048 B1 | 2/2002 | Chin et al. |
| 6,346,091 B1 | 2/2002 | Jacobsen et al. |
| 6,348,041 B1 | 2/2002 | Klint |
| 6,361,547 B1 | 3/2002 | Hieshima |
| 6,364,823 B1 | 4/2002 | Garibaldi et al. |
| 6,368,338 B1 | 4/2002 | Konya et al. |
| 6,371,972 B1 | 4/2002 | Wallace et al. |
| 6,375,606 B1 | 4/2002 | Garibaldi et al. |
| 6,375,628 B1 | 4/2002 | Zadno-Azizi et al. |
| 6,375,668 B1 | 4/2002 | Gifford et al. |
| 6,375,669 B1 | 4/2002 | Rosenbluth et al. |
| 6,379,329 B1 | 4/2002 | Naglreiter et al. |
| 6,379,374 B1 | 4/2002 | Hieshima et al. |
| 6,383,146 B1 | 5/2002 | Klint |
| 6,383,174 B1 | 5/2002 | Eder |
| 6,383,204 B1 | 5/2002 | Ferrera et al. |
| 6,383,205 B1 | 5/2002 | Samson et al. |
| 6,409,721 B1 | 6/2002 | Wheelock et al. |
| 6,416,535 B1 | 7/2002 | Lazarus |
| 6,416,541 B2 | 7/2002 | Denardo |
| 6,423,085 B1 | 7/2002 | Murayama et al. |
| 6,425,893 B1 | 7/2002 | Guglielmi |
| 6,425,914 B1 | 7/2002 | Wallace et al. |
| 6,428,557 B1 | 8/2002 | Hilaire |
| 6,428,558 B1 | 8/2002 | Jones et al. |
| 6,454,780 B1 | 9/2002 | Wallace |
| 6,458,119 B1 | 10/2002 | Berenstein et al. |

(56) References Cited

U.S. PATENT DOCUMENTS

| | | |
|---|---|---|
| 6,458,127 B1 | 10/2002 | Truckai et al. |
| 6,458,137 B1 | 10/2002 | Klint |
| 6,464,699 B1 | 10/2002 | Swanson |
| 6,468,266 B1 | 10/2002 | Bashiri et al. |
| 6,475,169 B2 | 11/2002 | Ferrera |
| 6,475,227 B2 | 11/2002 | Burke et al. |
| 6,478,773 B1 | 11/2002 | Gandhi et al. |
| 6,485,524 B2 | 11/2002 | Strecker |
| 6,494,884 B2 | 12/2002 | Gifford, III et al. |
| 6,500,149 B2 | 12/2002 | Gandhi et al. |
| 6,500,190 B2 | 12/2002 | Greene, Jr. et al. |
| 6,506,204 B2 | 1/2003 | Mazzocchi |
| 6,511,468 B1 | 1/2003 | Cragg et al. |
| 6,514,264 B1 | 2/2003 | Naglreiter |
| 6,530,934 B1 | 3/2003 | Jacobsen et al. |
| 6,533,801 B2 | 3/2003 | Wallace et al. |
| 6,537,293 B1 | 3/2003 | Berryman et al. |
| 6,540,657 B2 | 4/2003 | Cross, III et al. |
| 6,544,163 B2 | 4/2003 | Wallace et al. |
| 6,544,225 B1 | 4/2003 | Lulo et al. |
| 6,544,268 B1 | 4/2003 | Lazarus |
| 6,544,275 B1 | 4/2003 | Teoh |
| 6,547,804 B2 | 4/2003 | Porter et al. |
| 6,551,305 B2 | 4/2003 | Ferrera et al. |
| 6,551,340 B1 | 4/2003 | Konya et al. |
| 6,554,849 B1 | 4/2003 | Jones et al. |
| 6,558,367 B1 | 5/2003 | Cragg et al. |
| 6,569,179 B2 | 5/2003 | Teoh et al. |
| 6,572,628 B2 | 6/2003 | Dominguez et al. |
| 6,575,994 B1 | 6/2003 | Marin et al. |
| 6,585,748 B1 | 7/2003 | Jeffree |
| 6,585,754 B2 | 7/2003 | Wallace et al. |
| 6,589,227 B2 | 7/2003 | Sønderskov Klint |
| 6,589,230 B2 | 7/2003 | Gia et al. |
| 6,589,236 B2 | 7/2003 | Wheelock et al. |
| 6,589,265 B1 | 7/2003 | Palmer et al. |
| 6,592,605 B2 | 7/2003 | Lenker et al. |
| 6,602,261 B2 | 8/2003 | Greene, Jr. et al. |
| 6,602,269 B2 | 8/2003 | Wallace et al. |
| 6,603,994 B2 | 8/2003 | Wallace et al. |
| 6,605,101 B1 | 8/2003 | Schaefer et al. |
| 6,607,538 B1 | 8/2003 | Ferrera et al. |
| 6,607,539 B1 | 8/2003 | Hayashi et al. |
| 6,610,085 B1 | 8/2003 | Lazarus |
| 6,613,074 B1 | 9/2003 | Mitelberg et al. |
| 6,616,617 B1 | 9/2003 | Ferrera et al. |
| 6,620,152 B2 | 9/2003 | Guglielmi |
| 6,623,493 B2 | 9/2003 | Wallace et al. |
| 6,632,241 B1 | 10/2003 | Hancock et al. |
| 6,635,068 B1 | 10/2003 | Dubrul et al. |
| 6,635,069 B1 | 10/2003 | Teoh et al. |
| 6,638,291 B1 | 10/2003 | Ferrera et al. |
| 6,638,293 B1 | 10/2003 | Makower et al. |
| 6,656,173 B1 | 12/2003 | Palermo |
| 6,656,201 B2 | 12/2003 | Ferrera et al. |
| 6,656,218 B1 | 12/2003 | Denardo et al. |
| 6,656,351 B2 | 12/2003 | Boyle |
| 6,660,020 B2 | 12/2003 | Wallace et al. |
| 6,663,607 B2 | 12/2003 | Slaikeu et al. |
| 6,679,903 B2 | 1/2004 | Kurz |
| 6,685,653 B2 | 2/2004 | Ehr et al. |
| 6,689,141 B2 | 2/2004 | Ferrera et al. |
| 6,692,510 B2 | 2/2004 | West |
| 6,702,844 B1 | 3/2004 | Lazarus |
| 6,716,238 B2 | 4/2004 | Elliott |
| 6,723,112 B2 | 4/2004 | Ho et al. |
| 6,743,236 B2 | 6/2004 | Barry et al. |
| 6,743,251 B1 | 6/2004 | Eder |
| 6,766,219 B1 | 7/2004 | Hasey |
| 6,767,358 B2 | 7/2004 | Leonhardt et al. |
| 6,811,561 B2 | 11/2004 | Diaz et al. |
| 6,814,748 B1 | 11/2004 | Baker et al. |
| 6,835,185 B2 | 12/2004 | Ramzipoor et al. |
| 6,849,081 B2 | 2/2005 | Sepetka et al. |
| 6,852,116 B2 | 2/2005 | Leonhardt et al. |
| 6,853,418 B2 | 2/2005 | Suzuki et al. |
| 6,855,153 B2 | 2/2005 | Saadat |
| 6,855,155 B2 | 2/2005 | Denardo et al. |
| 6,860,893 B2 | 3/2005 | Wallace et al. |
| 6,860,901 B1 | 3/2005 | Baker et al. |
| 6,872,218 B2 | 3/2005 | Ferrera et al. |
| 6,878,163 B2 | 4/2005 | Denardo et al. |
| 6,905,503 B2 | 6/2005 | Gifford, III et al. |
| 6,913,618 B2 | 7/2005 | Denardo et al. |
| 6,929,654 B2 | 8/2005 | Teoh et al. |
| 6,945,956 B2 | 9/2005 | Waldhauser et al. |
| 6,958,061 B2 | 10/2005 | Truckai et al. |
| 6,958,068 B2 | 10/2005 | Hieshima |
| 6,964,657 B2 | 11/2005 | Cragg et al. |
| 6,966,892 B2 | 11/2005 | Gandhi et al. |
| 6,994,689 B1 | 2/2006 | Zadno-Azizi et al. |
| 6,994,711 B2 | 2/2006 | Hieshima et al. |
| 7,014,645 B2 | 3/2006 | Greene, Jr. et al. |
| 7,029,486 B2 | 4/2006 | Schaefer et al. |
| 7,029,487 B2 | 4/2006 | Greene, Jr. et al. |
| 7,033,374 B2 | 4/2006 | Schaefer et al. |
| 7,058,456 B2 | 6/2006 | Pierce |
| 7,060,083 B2 | 6/2006 | Gerberding |
| 7,070,607 B2 | 7/2006 | Murayama et al. |
| 7,147,618 B2 | 12/2006 | Kurz |
| 7,169,161 B2 | 1/2007 | Bonnette et al. |
| 7,182,774 B2 | 2/2007 | Barry et al. |
| 7,198,613 B2 | 4/2007 | Gandhi et al. |
| 7,238,194 B2 | 7/2007 | Monstadt et al. |
| 7,300,458 B2 | 11/2007 | Henkes et al. |
| 7,316,701 B2 | 1/2008 | Ferrera et al. |
| 7,323,000 B2 | 1/2008 | Monstdt et al. |
| 7,331,973 B2 | 2/2008 | Gesswein et al. |
| 7,344,558 B2 | 3/2008 | Lorenzo et al. |
| 7,410,482 B2 | 8/2008 | Murphy et al. |
| 7,422,569 B2 | 9/2008 | Wilson et al. |
| 7,473,266 B2 | 1/2009 | Glaser |
| 7,485,122 B2 | 2/2009 | Teoh |
| 7,485,317 B1 | 2/2009 | Murayama et al. |
| 7,524,322 B2 | 4/2009 | Monstdt et al. |
| 7,575,582 B2 | 8/2009 | Gandhi et al. |
| 7,578,826 B2 | 8/2009 | Gandhi et al. |
| RE41,029 E | 12/2009 | Guglielmi et al. |
| 7,691,124 B2 | 4/2010 | Balgobin |
| 7,708,755 B2 | 5/2010 | Davis, III et al. |
| 7,722,636 B2 | 5/2010 | Farnan |
| 7,722,637 B2 | 5/2010 | Barry et al. |
| 7,811,305 B2 | 10/2010 | Balgobin et al. |
| 7,879,064 B2 | 2/2011 | Monstdt et al. |
| 7,896,899 B2 | 3/2011 | Patterson et al. |
| 7,901,444 B2 | 3/2011 | Slazas |
| 7,918,872 B2 | 4/2011 | Mitelberg et al. |
| 8,267,955 B2 | 9/2012 | Patterson et al. |
| 2002/0010481 A1 | 1/2002 | Jayaraman |
| 2002/0065529 A1 | 5/2002 | Laurent et al. |
| 2002/0072712 A1 | 6/2002 | Nool et al. |
| 2002/0072791 A1 | 6/2002 | Eder et al. |
| 2002/0082620 A1 | 6/2002 | Lee |
| 2002/0087184 A1 | 7/2002 | Eder et al. |
| 2002/0120297 A1 | 8/2002 | Shadduck |
| 2002/0128671 A1 | 9/2002 | Wallace et al. |
| 2002/0138095 A1 | 9/2002 | Mazzocchi et al. |
| 2002/0143349 A1 | 10/2002 | Gifford et al. |
| 2002/0169473 A1 | 11/2002 | Sepetka et al. |
| 2003/0014073 A1 | 1/2003 | Bashiri et al. |
| 2003/0040733 A1 | 2/2003 | Cragg et al. |
| 2003/0045901 A1 | 3/2003 | Opolski |
| 2003/0083676 A1 | 5/2003 | Wallace |
| 2003/0130689 A1 | 7/2003 | Wallace et al. |
| 2003/0169473 A1 | 9/2003 | Cotter et al. |
| 2003/0171770 A1 | 9/2003 | Kusleika et al. |
| 2003/0176857 A1 | 9/2003 | Lee |
| 2003/0181927 A1 | 9/2003 | Wallace |
| 2003/0225365 A1 | 12/2003 | Greff et al. |
| 2004/0002731 A1 | 1/2004 | Aganon et al. |
| 2004/0002732 A1 | 1/2004 | Teoh et al. |
| 2004/0002733 A1 | 1/2004 | Teoh |
| 2004/0024394 A1 | 2/2004 | Wallace et al. |
| 2004/0034363 A1 | 2/2004 | Wilson et al. |

(56) References Cited

U.S. PATENT DOCUMENTS

| | | |
|---|---|---|
| 2004/0034378 A1 | 2/2004 | Monstadt et al. |
| 2004/0078050 A1 | 4/2004 | Monstadt et al. |
| 2004/0098029 A1 | 5/2004 | Teoh et al. |
| 2004/0106946 A1 | 6/2004 | Ferrera et al. |
| 2004/0170685 A1 | 9/2004 | Carpenter et al. |
| 2004/0181256 A1 | 9/2004 | Glaser |
| 2004/0193178 A1 | 9/2004 | Nikolchev |
| 2004/0193206 A1 | 9/2004 | Gerberding et al. |
| 2004/0220563 A1 | 11/2004 | Eder |
| 2004/0220585 A1 | 11/2004 | Nikolchev |
| 2004/0225279 A1 | 11/2004 | Raymond |
| 2005/0021023 A1 | 1/2005 | Guglielmi et al. |
| 2005/0079196 A1 | 4/2005 | Henkes et al. |
| 2005/0222603 A1 | 10/2005 | Andreas et al. |
| 2006/0025801 A1 | 2/2006 | Lulo et al. |
| 2006/0025802 A1 | 2/2006 | Sowers |
| 2006/0036281 A1 | 2/2006 | Patterson et al. |
| 2006/0079926 A1* | 4/2006 | Desai et al. .................. 606/200 |
| 2006/0116714 A1 | 6/2006 | Sepetka et al. |
| 2006/0135986 A1 | 6/2006 | Wallace et al. |
| 2006/0271097 A1* | 11/2006 | Ramzipoor et al. ......... 606/200 |
| 2006/0276824 A1 | 12/2006 | Mitelberg et al. |
| 2007/0055302 A1 | 3/2007 | Henry et al. |
| 2007/0173757 A1 | 7/2007 | Levine et al. |
| 2007/0185524 A1 | 8/2007 | Diaz et al. |
| 2007/0239193 A1* | 10/2007 | Simon et al. ................ 606/191 |
| 2008/0045922 A1 | 2/2008 | Cragg et al. |
| 2008/0045997 A1 | 2/2008 | Balgobin et al. |
| 2008/0051803 A1 | 2/2008 | Monjtadt et al. |
| 2008/0086163 A1* | 4/2008 | Jones et al. ................. 606/191 |
| 2008/0097462 A1 | 4/2008 | Mitelberg et al. |
| 2008/0103585 A1 | 5/2008 | Monstadt et al. |
| 2008/0125855 A1 | 5/2008 | Henkes et al. |
| 2008/0220216 A1 | 9/2008 | Unger et al. |
| 2008/0228215 A1 | 9/2008 | Strauss et al. |
| 2008/0228216 A1 | 9/2008 | Strauss et al. |
| 2008/0243106 A1 | 10/2008 | Coe et al. |
| 2008/0300616 A1 | 12/2008 | Que et al. |
| 2008/0306504 A1 | 12/2008 | Win et al. |
| 2008/0319532 A1 | 12/2008 | Monstadt et al. |
| 2009/0177261 A1 | 7/2009 | Teoh et al. |
| 2009/0182268 A1 | 7/2009 | Thielen et al. |
| 2009/0254111 A1 | 10/2009 | Monstadt et al. |
| 2009/0254169 A1 | 10/2009 | Spenser et al. |
| 2009/0270877 A1 | 10/2009 | Johnson et al. |
| 2009/0312748 A1 | 12/2009 | Johnson et al. |
| 2010/0004673 A1 | 1/2010 | Denison et al. |
| 2010/0023105 A1 | 1/2010 | Levy et al. |
| 2010/0030200 A1 | 2/2010 | Strauss et al. |
| 2010/0049165 A1 | 2/2010 | Sutherland et al. |
| 2010/0076479 A1 | 3/2010 | Monstadt |
| 2010/0174269 A1 | 7/2010 | Tompkins et al. |
| 2011/0022003 A1 | 1/2011 | Tekulve |
| 2011/0098814 A1 | 4/2011 | Monstadt et al. |
| 2011/0118777 A1 | 5/2011 | Patterson et al. |
| 2011/0172700 A1 | 7/2011 | Bose et al. |
| 2012/0041470 A1 | 2/2012 | Shrivastava et al. |
| 2012/0065720 A1 | 3/2012 | Strauss et al. |
| 2012/0116442 A1 | 5/2012 | Monstadt et al. |
| 2012/0226305 A1 | 9/2012 | Strauss et al. |
| 2012/0313447 A1 | 12/2012 | Park et al. |

FOREIGN PATENT DOCUMENTS

| | | |
|---|---|---|
| DE | 69627243 | 1/1997 |
| DE | 19547617 | 9/1997 |
| DE | 19607451 | 9/1997 |
| DE | 19610333 | 9/1997 |
| DE | 19647280 | 5/2001 |
| DE | 19952387 | 5/2001 |
| DE | 10010840 | 9/2001 |
| DE | 10118017 | 10/2002 |
| DE | 10155191 | 5/2003 |
| DE | 10337000 | 3/2005 |
| EP | 0368571 A2 | 5/1990 |
| EP | 707830 | 4/1996 |
| EP | 711 532 | 5/1996 |
| EP | 717969 A2 | 6/1996 |
| EP | 720 838 | 7/1996 |
| EP | 765636 A3 | 7/1997 |
| EP | 0792623 | 9/1997 |
| EP | 0800791 | 10/1997 |
| EP | 820 726 | 1/1998 |
| EP | 830 873 | 3/1998 |
| EP | 829236 A1 | 3/1998 |
| EP | 853 955 | 7/1998 |
| EP | 865 773 | 9/1998 |
| EP | 882 428 | 9/1998 |
| EP | 904 737 | 3/1999 |
| EP | 914 807 | 5/1999 |
| EP | 941 700 | 9/1999 |
| EP | 941 701 | 9/1999 |
| EP | 992 220 | 4/2000 |
| EP | 1005837 A2 | 6/2000 |
| EP | 1 120 088 | 8/2001 |
| EP | 1 125 553 | 8/2001 |
| EP | 1 129 666 | 9/2001 |
| EP | 1 142 535 | 10/2001 |
| EP | 1 169 969 | 1/2002 |
| EP | 1 188 413 | 3/2002 |
| EP | 1 188 414 | 3/2002 |
| EP | 1 312 312 | 5/2003 |
| EP | 1 316 293 | 6/2003 |
| EP | 1 358 850 | 11/2003 |
| EP | 1 669 032 | 6/2006 |
| EP | 1738698 A2 | 1/2007 |
| EP | 832 607 | 4/2008 |
| JP | 6-246004 | 9/1994 |
| JP | 7-155331 | 6/1995 |
| JP | 7-265431 | 10/1995 |
| JP | 7-284534 | 10/1995 |
| JP | 9-168541 A | 6/1997 |
| JP | 10-201766 | 8/1998 |
| JP | 11-47138 | 2/1999 |
| JP | 11-76249 | 3/1999 |
| JP | 2001-513389 A | 9/2001 |
| JP | 2002-523172 A | 7/2002 |
| JP | 2004-500929 A | 1/2004 |
| JP | 2006-051349 A | 2/2006 |
| JP | 2008-525113 A | 7/2008 |
| WO | WO-88/03817 | 6/1988 |
| WO | WO-89/06984 | 8/1989 |
| WO | WO-90/12616 | 11/1990 |
| WO | WO-91/13592 | 9/1991 |
| WO | WO-92/14408 | 9/1992 |
| WO | WO-92/21400 | 12/1992 |
| WO | WO-93/11719 | 6/1993 |
| WO | WO-93/16650 | 9/1993 |
| WO | WO-94/06502 A2 | 3/1994 |
| WO | WO-94/06503 | 3/1994 |
| WO | WO-94/10936 | 5/1994 |
| WO | WO-94/11051 | 5/1994 |
| WO | WO-94/26175 | 11/1994 |
| WO | WO-95/12367 | 5/1995 |
| WO | WO-96/18343 | 6/1996 |
| WO | WO-96/32153 | 10/1996 |
| WO | WO-96/39950 | 12/1996 |
| WO | WO-97/27888 | 8/1997 |
| WO | WO-97/42881 | 11/1997 |
| WO | WO-98/09570 | 3/1998 |
| WO | WO 98/17183 | 4/1998 |
| WO | WO-98/33452 | 8/1998 |
| WO | WO-98/34546 | 8/1998 |
| WO | WO-98/39048 A2 | 9/1998 |
| WO | WO-98/58590 | 12/1998 |
| WO | WO-99/02094 | 1/1999 |
| WO | WO-99/05977 | 2/1999 |
| WO | WO-99/07292 | 2/1999 |
| WO | WO-99/09893 | 3/1999 |
| WO | WO-99/32037 | 7/1999 |
| WO | WO-99/40852 | 8/1999 |
| WO | WO-99/42038 | 8/1999 |
| WO | WO-99/44538 | 9/1999 |

(56) References Cited

FOREIGN PATENT DOCUMENTS

| | | |
|---|---|---|
| WO | WO-99/51151 | 10/1999 |
| WO | WO-99/56636 | 11/1999 |
| WO | WO-99/49812 A3 | 12/1999 |
| WO | WO-00/12016 | 3/2000 |
| WO | WO-00/13593 | 3/2000 |
| WO | WO-00/25680 | 5/2000 |
| WO | WO-00/44306 | 8/2000 |
| WO | WO-00/72781 A2 | 12/2000 |
| WO | WO-01/32085 | 5/2001 |
| WO | WO-01/56500 A2 | 8/2001 |
| WO | WO-01/58365 | 8/2001 |
| WO | WO-01/58382 A2 | 8/2001 |
| WO | WO-01/87184 | 11/2001 |
| WO | WO-01/93937 A2 | 12/2001 |
| WO | WO-02/02018 | 1/2002 |
| WO | WO-02/13705 | 2/2002 |
| WO | WO-02/13706 A2 | 2/2002 |
| WO | WO-02/32496 | 4/2002 |
| WO | WO-02/39911 A2 | 5/2002 |
| WO | WO-02/41753 A2 | 5/2002 |
| WO | WO-02/45596 A2 | 6/2002 |
| WO | WO-02/054943 A2 | 7/2002 |
| WO | WO-02/054980 A2 | 7/2002 |
| WO | WO-02/072168 A2 | 9/2002 |
| WO | WO-02/087449 | 11/2002 |
| WO | WO-02/087651 | 11/2002 |
| WO | WO-02/089676 A2 | 11/2002 |
| WO | WO-02/096273 A2 | 12/2002 |
| WO | WO-02/096301 | 12/2002 |
| WO | WO-03/001970 A2 | 1/2003 |
| WO | WO-03/007823 | 1/2003 |
| WO | WO-03/017852 | 3/2003 |
| WO | WO-03/034927 | 5/2003 |
| WO | WO-03/039624 A2 | 5/2003 |
| WO | WO-03/041615 | 5/2003 |
| WO | WO-03/053257 | 7/2003 |
| WO | WO-03/053281 | 7/2003 |
| WO | WO-03/072179 | 9/2003 |
| WO | WO-03/073914 A2 | 9/2003 |
| WO | WO-03/077776 | 9/2003 |
| WO | WO-03/077984 | 9/2003 |
| WO | WO-03/082128 | 10/2003 |
| WO | WO-03/086240 | 10/2003 |
| WO | WO-03/092547 | 11/2003 |
| WO | WO-03/099370 | 12/2003 |
| WO | WO-2004/008974 | 1/2004 |
| WO | WO-2004/014239 | 2/2004 |
| WO | WO-2004/069059 | 8/2004 |
| WO | WO-2004/073529 | 9/2004 |
| WO | WO-2005/113035 A2 | 12/2005 |
| WO | WO-2006/032291 | 3/2006 |
| WO | WO-2006/069123 | 6/2006 |
| WO | WO-2007/121405 | 10/2007 |
| WO | WO-2008/112435 | 9/2008 |
| WO | WO-2008/112436 | 9/2008 |
| WO | WO-2010/117883 | 10/2010 |
| WO | WO-2010/123821 | 10/2010 |

OTHER PUBLICATIONS

Henkes et al., Neurosurgery 54, No. 2, 268 (2004).

Middleton, J.C. & Tipton, A.J. Synthetic biodegradable polymers as orthopedic devices, Biomaterials 21, 2335-46 (2000).

* cited by examiner

IMPLANT INCLUDING A COIL AND A STRETCH-RESISTANT MEMBER

RELATED APPLICATIONS

This application is a continuation of U.S. application Ser. No. 12/038,730, filed Feb. 27, 2008, which claims the benefit under 35 U.S.C. §119(e) of provisional application Ser. No. 60/894,589 filed Mar. 13, 2007 and 60/894,858 filed on Mar. 14, 2007, each of the above applications being expressly incorporated herein by reference in its entirety.

FIELD OF THE INVENTION

This invention relates to implantable coils and, more particularly, to a coil implant having a stretch-resistant member internal to the coil.

BACKGROUND OF THE INVENTION

Implants are delivered to a vascular site, such as an aneurysm, of a patient via a microcatheter to occlude or embolize the vascular site. Typically, the implant is engaged at the distal end of either the delivery microcatheter or the guidewire contained within the microcatheter and controllably released therefrom into the vascular site to be treated. The clinician delivering the implant must navigate the microcatheter or guide catheter through the vasculature and, in the case of intracranial aneurysms, navigation of the microcatheter is through tortuous microvasculature. This delivery may be visualized by fluoroscopy or another suitable means. Once the distal tip of the catheter or guidewire is placed in the desired vascular site, the clinician must then begin to articulate the implant in the vascular site to ensure that the implant will be positioned in a manner to sufficiently embolize the site. Once the implant is appropriately positioned, the clinician must then detach the implant from the catheter or guidewire without distorting the positioning of the implant. Detachment may occur through a variety of means, including, chemical detachment, mechanical detachment, hydraulic detachment, and thermal detachment.

The procedure of delivering the implant to the vascular site can be complicated for a number of reasons. One common complication found with implants of the art is that the doctor is not able to effectively articulate, rotate, and/or control the implant during positioning in the vascular site to provide sufficient embolization. One reason that the implant may not be able to effectively articulate is that the proximate portion of the implants of the art are often rigid. This portion is referred to as the "stiff zone" and may also contain the detachment mechanism. One drawback of an implant having a "stiff zone" is that this "stiff zone" may cause catheter kick-out after deployment of the implant to the vascular site.

Another complication with implants of the art is that the implant may not be able to substantially conform to the vascular site due the presence of a stretch-resistant member. For example, U.S. Pat. No. 5,582,619 teaches a stretch-resistant member that is fixedly attached at both ends or at one end and then at another point in the lumen of the catheter. Due to the stretch-resistant member being fixedly attached in two locations, the implant, after delivery, will maintain some stretch-resistant properties. If the implant is stretch resistant after delivery, this may inhibit the implant's ability to substantially conform to the vascular site.

Yet another complication with implants of the art is that after detachment, the implant may contain a traumatic (or sharp) portion or stem. This traumatic portion most frequently occurs with implants that are mechanically or electrolytically detached from the delivery device. See, for example, U.S. Publ. 2004/0034363 which describes use of a stretch-resistant member and a loop at the proximal end of the coil. The loop, after deployment, is a traumatic portion. The traumatic portion may cause damage to the patient in the surrounding vasculature. Further, it is also contemplated that due to the presence of the loop, the clinician is not able to torque the implant during delivery therefore making the appropriate placement more difficult.

In light of the above, there exists a need for an implant that maintains the ability to freely articulate and torque without having a "stiff zone," and also for the implant to substantially conform to the vascular site. There also exists a need to have an implant without a traumatic portion or stem after detachment at the vascular site.

SUMMARY OF THE INVENTION

The invention is directed to, in one embodiment, an implant with a stretch-resistant member.

The implant further includes a member for engaging a positioning device or a positioner. The member for engaging a positioning device and the stretch-resistant member are coupled together. The member for engaging a positioning device is free to move with respect to the coil thereby allowing for the implant to articulate and be positioned more accurately. In one embodiment, the implant includes a primary coil that defines a lumen disposed on an axis. A proximal end of the primary coil defines a proximal aperture, and a distal end of the primary coil defines a distal aperture. A stretch-resistant member is disposed in the lumen, with a coupling portion of the stretch-resistant member coupled in the lumen to the member for engaging a positioning device that has an engagement portion exterior to the lumen. The stretch-resistant member can be a line, a filament, or a braid.

The implant optionally can include a secondary coil. In one embodiment, the secondary coil is disposed at least in part in the lumen, and that further defines the proximal aperture. The secondary coil is coaxial with the primary coil.

The coupling portion of the stretch-resistant member can be coupled to a distal end of the member for engaging a positioning device which can preferably be an eyelet. The stretch-resistant member can also couple to the engagement member with a wrap or a knot, and can also extend back to the distal end of the primary coil so that two lengths of line extend along the length of the lumen. The line can also have an end that engages a retainer at the distal end of the primary coil. In one embodiment, the retainer is ball-shaped or rounded.

The member for engaging a positioning device can preferably be a rod and have a proximal end with an engagement portion, and the engagement portion can preferably be a ball mounted on the proximal end of the member for engaging a positioning device. The member for engaging a positioning device can also extend through the proximal aperture so that the engagement portion is disposed at the proximal-most end of the implant. The member for engaging a positioning device and the coupling portion of the stretch-resistant member can be freely disposed at the proximal end of the implant so that the member for engaging a positioning device and the coupling portion are not connected to or attached to the primary or secondary coils. Also, the member for engaging a positioning device can have a central axis that intersects the proximal aperture at various points. The member and engagement portion are free to move distally into the lumen of the primary (or primary and secondary) coil. In one embodiment, the member and engagement portion can move distally to be completely in the lumen of the coil.

In another embodiment, the invention is directed to a method of embolizing vascular site in a patient. The implant is introduced to the vascular site via a positioner and then detached from the positioner thereby embolizing the vascular site. The implant can be detached from the positioner by chemical detachment, electrolytic detachment, mechanical detachment, hydraulic detachment, or thermal detachment. After detachment, the engagement portion is contained within the interior lumen. In one embodiment, the engagement portion is completely contained within the interior lumen.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

DETAILED DESCRIPTION OF THE INVENTION

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications and patent applications cited herein are incorporated herein by reference in their entirety. Nothing herein is to be construed as an admission that the invention is not entitled to antedate such disclosure by virtue of prior invention.

It must be noted that as used herein and in the appended claims, the singular forms "a," "an," and "the" include plural references unless the context clearly dictates otherwise.

Methods of Embolizing a Vascular Site

Prior to describing the embodiments of the implant of the invention, provided below is an embodiment of the invention related to embolizing a vascular site of a patient using an implant.

Figure 1A:
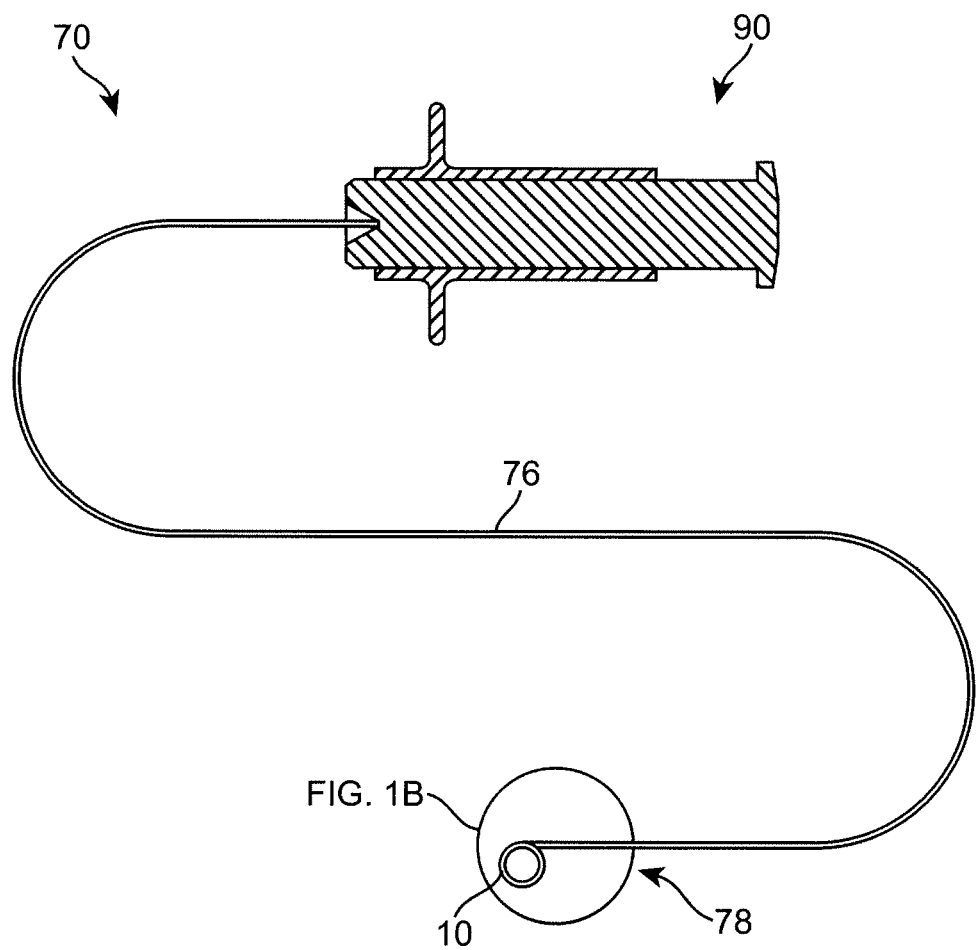
FIG 1A is a plan view of an exemplary positioning system and a plan view of an exemplary implant.
Figure 1B:
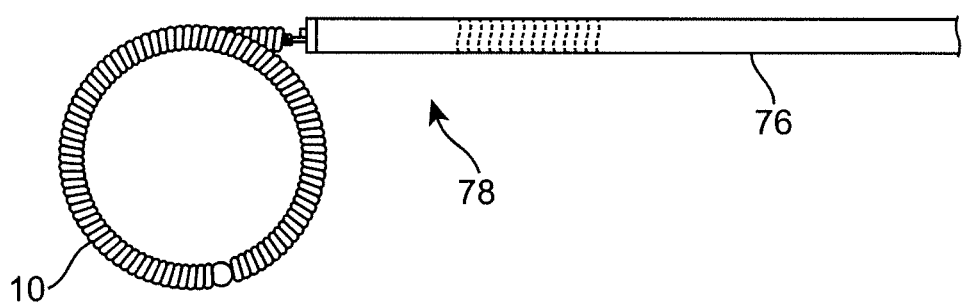
FIG. 1B is a closer view of a portion of FIG. 1A.

As illustrated in FIGS. 1A and 1B, the implant of the invention, in one embodiment, may be used with a positioning device 70 that may optionally include an actuator 90 operated by an operator, a positioning tube 76 engaging the actuator 90, and an implant interface 78 at the distal end of the positioning tube 76. A portion of the implant interface 78 engages a complementary portion of an implant 10. The positioning device 70 is more specifically described below in FIG. 3.

Figure 2:
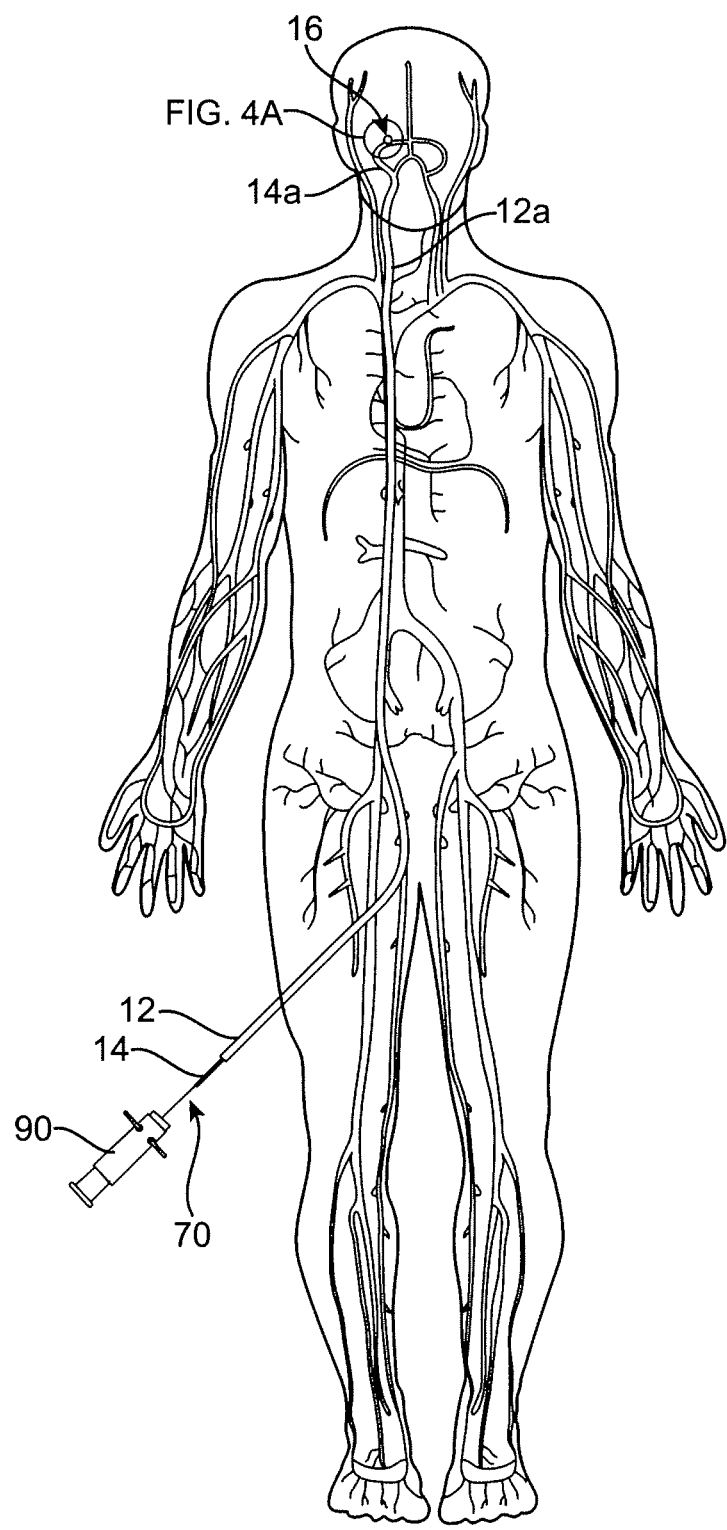
FIG. 2 is a plan view of a positioning system of FIG. 1 within the human body.

In the embodiment illustrated in FIGS. 1A and 1B, an operator uses a guide tube or guide catheter 12 to position a delivery tube or microcatheter 14 in a patient's vasculature, as illustrated in FIG. 2. The procedure involves inserting the guide catheter 12 into the patient's vasculature through an access point such as the groin, and directing the distal end 12a of the guide catheter 12 through the vascular system until it reaches the carotid artery. After removing a guide wire (not shown) from the guide catheter 12, a microcatheter 14 is inserted into the guide catheter 12 and the distal end 14a of the microcatheter 14 subsequently exits the guide catheter distal end 12a and is positioned near the target site 16, such as an aneurysm in the patient's brain.

Figure 4A:
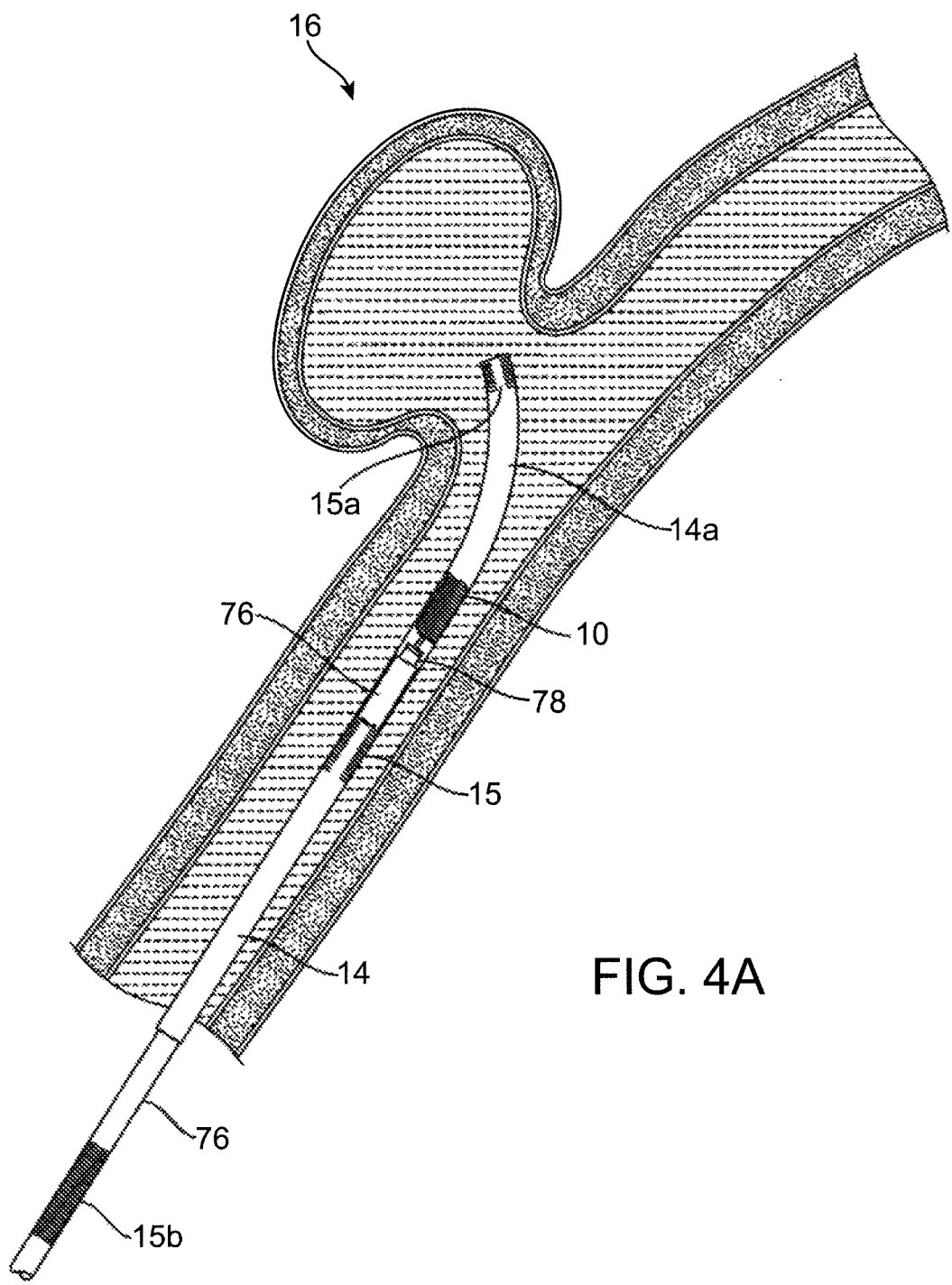
FIG. 4A is a closer view of a portion of FIG. 2 showing the positioning system in partial cross-section and an exemplary implant in a position within the human body prior to deployment of the implant.
Figure 4B:
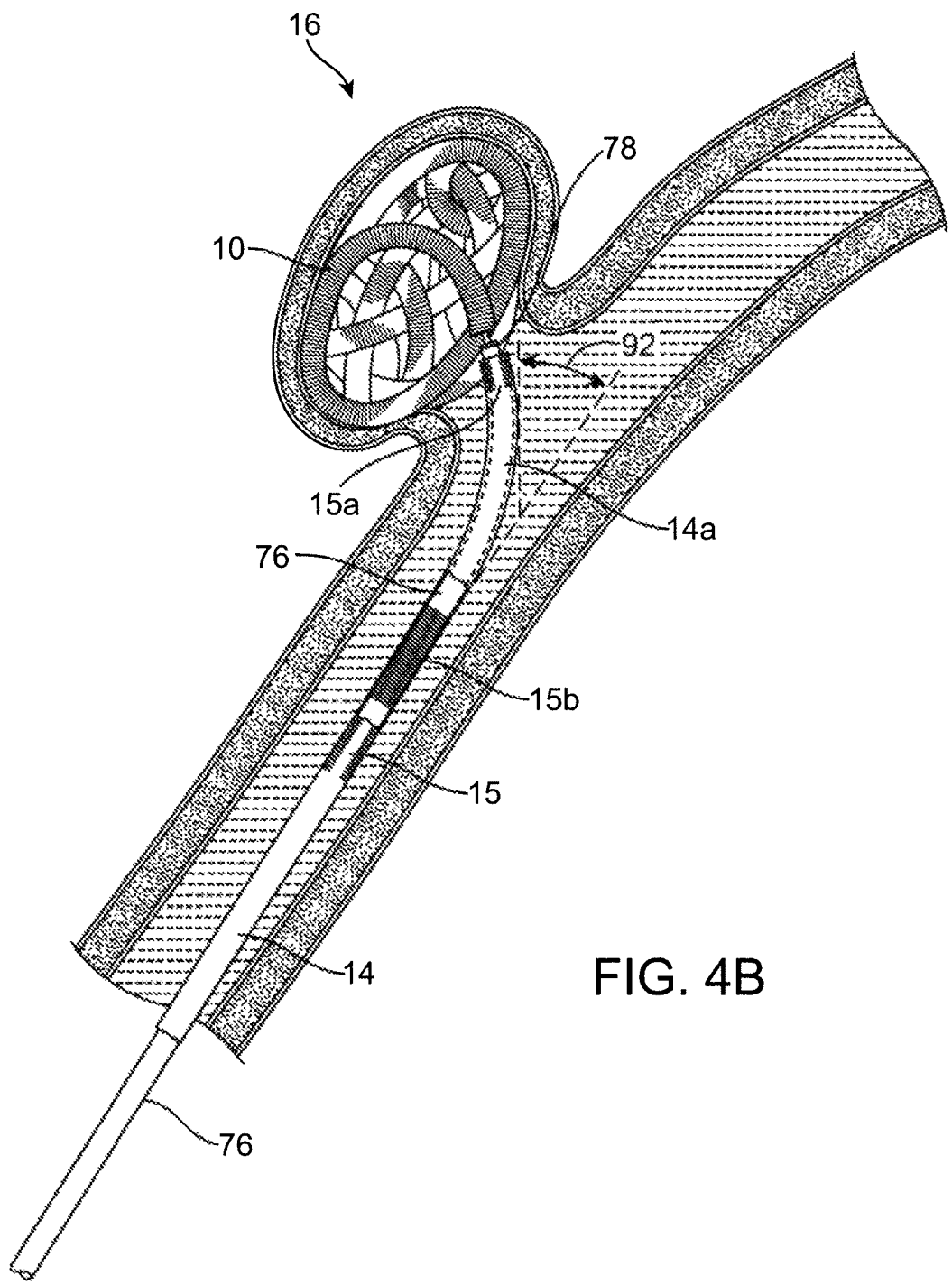
FIG. 4B is a closer view of a portion of FIG. 2 showing the positioning system in partial cross-section and an exemplary implant in another position within the human body after deployment but before detachment.

As illustrated in FIGS. 4A and 4B, the microcatheter 14 includes microcatheter markers 15 and 15a that facilitate imaging of the distal end 14a of the microcatheter 14 with common imaging systems and, in the illustrated embodiment, the microcatheter markers 15 and 15a are made of a radiopaque material. After the distal end 14a reaches the target site 16, the positioning device 70 (as shown in FIG. 1A) of the illustrated embodiment is then inserted into the microcatheter 14 to position the implant interface 78 at the distal end of the positioning device 70 near the target site 16, as illustrated in FIG. 4B.

If the implant 10 is being delivered in the procedure, the implant 10 is attached to the implant interface 78 prior to inserting the positioning device 70 into the microcatheter 14. This mode of implant delivery is illustrated in FIGS. 2 and 4A-B. The delivery of the implant 10 is facilitated by disposing the microcatheter marker 15a near the target site 16, and aligning the microcatheter marker 15 with a positioner marker 15b in the positioner tube 76 which, when the two markers (markers 15 and 15b) are aligned with each other as illustrated in FIG. 4B, indicates to the operator that the implant interface 78 is in the proper position for the release of the implant 10 from the positioning device 70. After depositing the implant 10 at the target site 16, a second implant 10 can be deposited at the target site 16 by removing the positioning device 70 from the microcatheter 14 and inserting a second positioning device 70 with an attached second implant 10 into the microcatheter 14 in a manner similar to the method used with the insertion of the first implant 10. The same procedure can be used for a third implant 10 and subsequent implants if clinically necessary. If the implant 10 is already in the patient's body to be retrieved or repositioned, the positioning device 70 is inserted into the microcatheter 14 without the implant 10.

As can be seen in FIG. 4A and FIG. 4B, it is advantageous that the implant 10 and positioning device 70 (not shown) have a reduced "stiff zone" at the interface 78 to better allow delivery through the tortuous vasculature, responsive placement into the target site 16, and for the ability to reposition the implant 10.

Implant and Device Configurations

The implant of the invention maintains a high level of articulation, including the ability to torque, prior to deployment thereby providing responsive placement and repositioning prior to deployment. This level of articulation is partially due to a lack of having or having a very small "stiff zone" in its proximal end. Further and as explained below, in one embodiment, the implant of the invention is stemless after detachment. As a result of the implant being stemless, the level of trauma associated with deployment of an implant in the vasculature is minimized.

Additionally, as described below, the implant of the invention has a stretch-resistant member and this feature eases delivery by allowing the clinician to reposition as necessary without the implant deforming while maintaining its secondary shape. After the implant of the invention is delivered, the implant of the invention no longer retains its "stretch resistance" properties thereby allowing the implant to better substantially conform to the vascular site.

Figure 3:
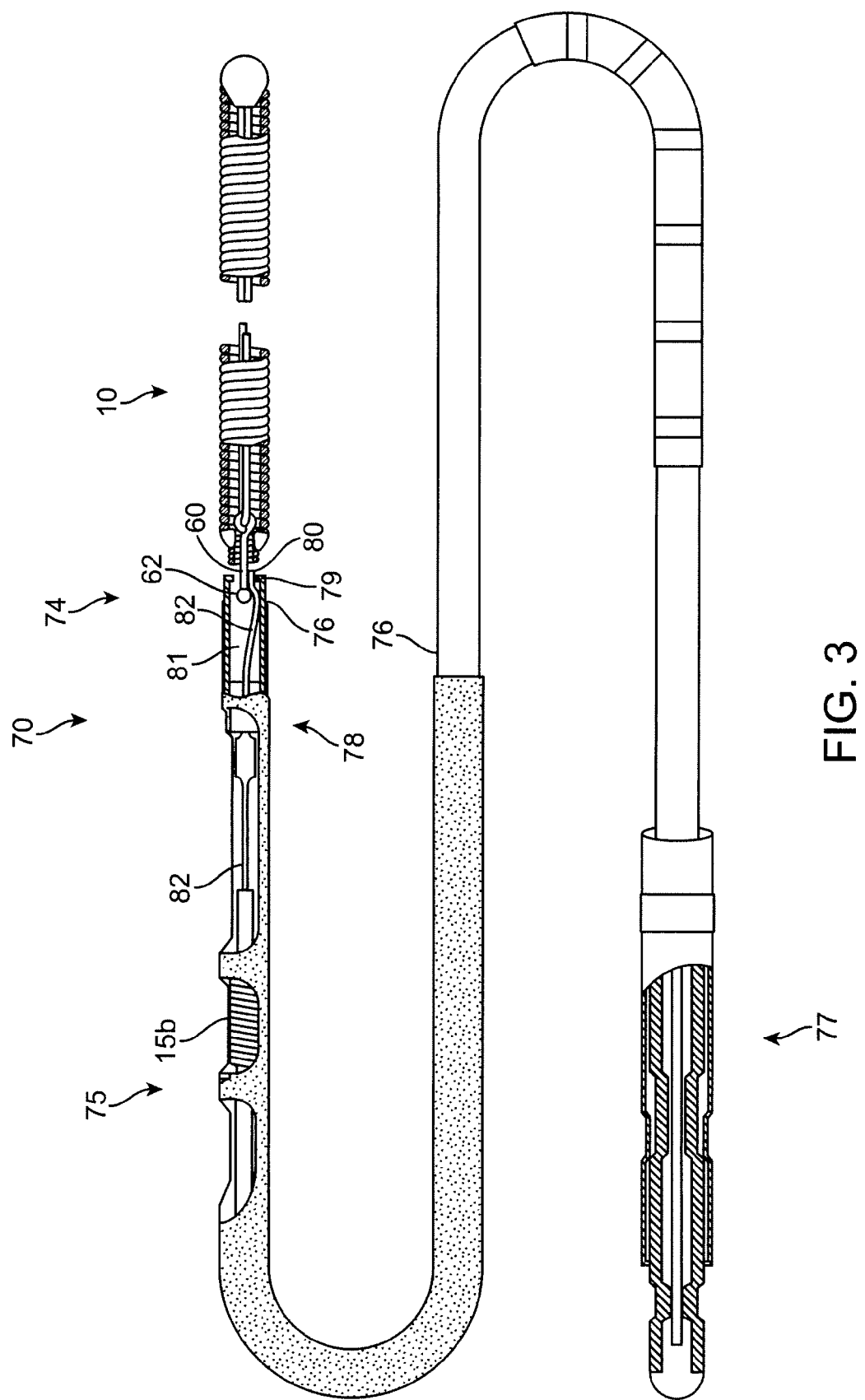
FIG. 3 is a partial cross-sectional plan view of the implant of FIG. 1 with an exemplary positioning device.
Figure 5:
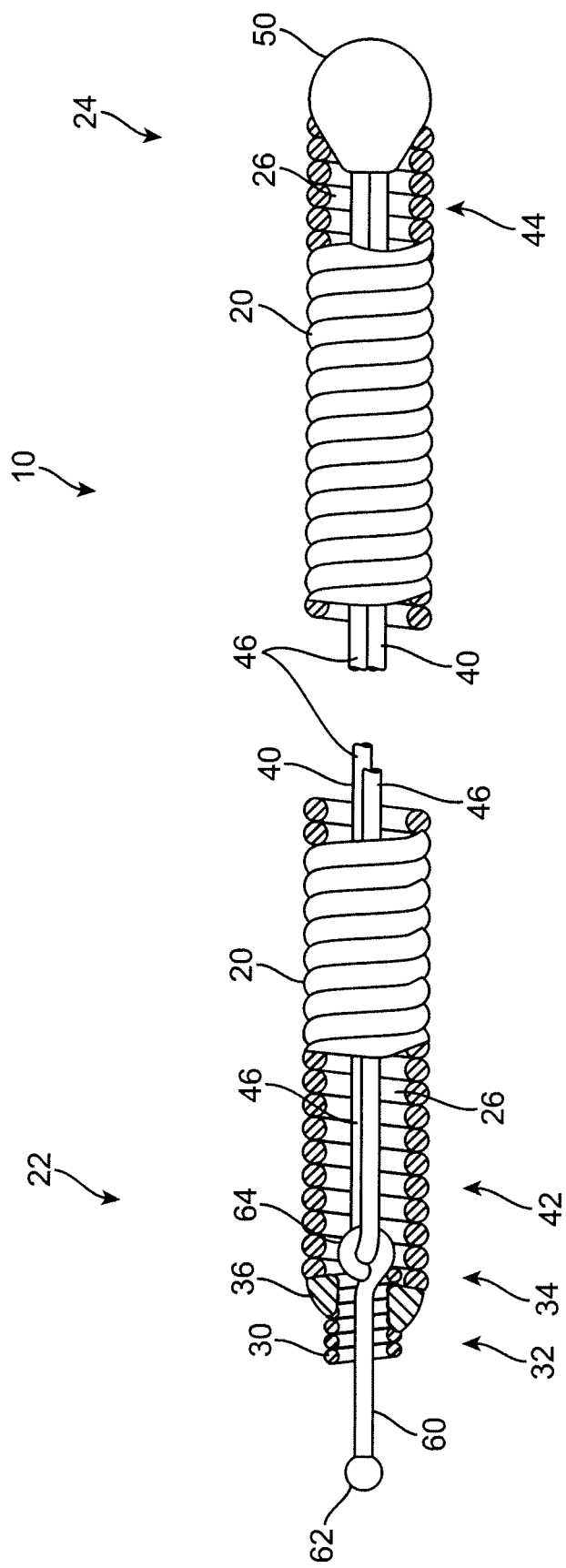
FIG. 5 is a partial cross-sectional plan view of an implant with a stretch-resistant member in partial cross-section.

The implant 10 illustrated in FIG. 5 includes a primary coil 20, a secondary coil 30, a stretch-resistant member 40, a retainer 50, and a member 60 for engaging a positioning device 70 (shown in FIGS. 1A, 1B, and 3). The member 60 for engaging a positioning device 70 is preferably a rod that includes a ball 62 and an eyelet 64.

The primary coil 20 has a proximal end 22 and a distal end 24 defining an internal lumen 26 extending between the ends of the primary coil. The primary coil 20 can be formed in a variety of shapes once heat setting of the coil form is performed. One such shape of the primary coil can be found in U.S. Ser. No. 12/038,737, filed on even date herewith and titled "An implant, a mandrel, and a method of forming an implant." This application is incorporated by reference into its entirety.

The optional secondary coil 30 is disposed at the proximal end 22 of the primary coil 20 and further defines the proximal aperture. In one embodiment, the secondary coil 30 has an outer diameter that is sized to fit within the internal lumen 26 of the primary coil 20 and the primary coil 20 partially envelops the secondary coil 30. In this embodiment, the secondary coil 30 has an outer diameter which is less than the inner diameter of the primary coil 20. In another embodiment, the secondary coil 30 has an outer diameter equal or less than the outer diameter of the primary coil 20. In another embodiment, the secondary coil 30 is adjacent to the primary coil 20. The secondary coil 30 may be affixed by any means, such as welded, to the proximal end 22 of the primary coil 20 with weld 36, with a distal portion 34 of the secondary coil 30 disposed within the internal lumen 26 and a proximal portion 32 disposed proximal to the primary coil 20.

The retainer 50 engages the distal end 24 of the primary coil 20. The retainer 50, if present, is shaped such that there is minimized trauma to the vascular site upon delivery. In certain embodiments, the retainer 50 is ball-shaped. In some embodiments, the retainer 50 is rounded on the portion that is exterior to the lumen 26 and the diameter of the retainer 50 is equal to or slightly less that than the outer diameter of the primary coil 20. The stretch-resistant member 40 is disposed in the internal lumen 26. A distal end 44 of the stretch-resistant member engages the retainer 50. A proximal end 42 of the stretch-resistant member 40 engages the eyelet 64 of the rod 60. The distal portion of the rod 60 and the eyelet 64 are disposed in the internal lumen 26. A proximal portion of the rod 60 and the ball 62 extends proximally from the internal lumen 26 and is disposed proximal to the primary and secondary coils 20 and 30. The rod 60 and the proximal end 42 of the stretch-resistant member 40 are not connected to or attached to the primary or secondary coils 20 and 30 and are free to move within the internal lumen 26 in the direction of the longitudinal axis of the implant 10 and to move so that the rod 60 can assume an angle relative to the longitudinal axis of the implant 10.

Figure 7:
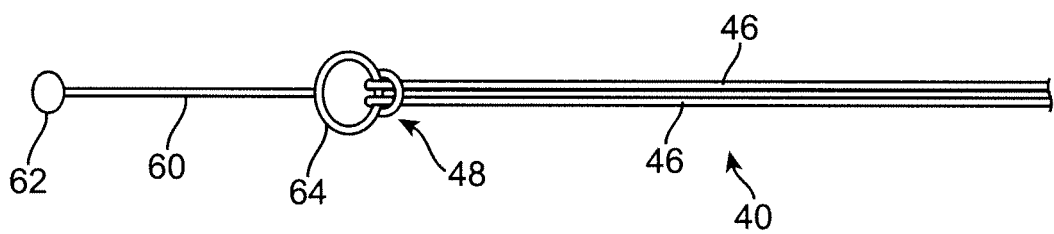
FIG. 7 is a plan view of an embodiment of the stretch-resistant member of FIG. 5.

The proximal end 42 of the stretch-resistant member 40 and the eyelet 64 form a coupling that can comprise any type of connection. The stretch-resistant member 40 is preferably a single line 46 that extends from the retainer 50 to the eyelet 64, passes through the eyelet 64, and extends from the eyelet 64 to the retainer 50. The line 46 can also be a filament or a braid. When passing through the eyelet 64, the line 46 is preferably wrapped through the eyelet 64 to form a knot 48, and is most preferably formed as a hitch knot as illustrated in FIG. 7. Alternatively, the line 46 can be one or more separate lines that terminate at the eyelet 64 to form a coupling with the eyelet 64. In another alternative, the coupling can be formed in the stretch-resistant member 40 in a middle portion disposed between proximal and distal portions of the stretch-resistant member 40, such as with a knot coupling the proximal and distal portions of the stretch-resistant member 40 together within the internal lumen 26. In yet another alternative, the coupling can be a combination of a knot and a wrapping, or a combination of multiple lines 46 employing different couplings. The coupling can also involve the modification of the stretch-resistant member 40 at the point of coupling, such as by deforming or melting of the stretch-resistant member 40 to join the end of a line 46 back onto itself to form a closed loop. In still another alternative, an eyelet can be formed at the proximal end of the stretch-resistant member 40 that is coupled to the distal end of the rod 60, with the distal end of the rod 60 knotted to form the coupling, or with the distal end of the rod 60 deformed or melted back onto itself to form a closed loop.

The inner diameter of the secondary coil 30 is selected to engage the eyelet 64 and to engage the positioning device 70 (shown in FIG. 1A).

The rod 60 can have various cross-sectional shapes, such as a circular or triangular shape. The ball 62 can be replaced with another structure such as a disc, hook, or ring structure that preferably provides an external diameter or equivalent dimension comparable to the ball 62.

Fibers

The primary coil 20, secondary coil 30, and the stretch-resistant member 40 can also comprise at least one fiber 85. The fiber(s) 85 can be a plurality of fibers, at least one bundle of fibers, or a plurality of fiber bundles. The fiber(s) 85 can be enlaced, tied, or knotted to a number of places on the implant 10. The fibers or fiber bundles 85 can be disposed so that they are not tied or knotted to the implant 10, thereby avoiding potentially obstructive bundles that might hinder deployment of the implant 10 or might mechanically damage the implant 10. The use of fibers with coils is disclosed in U.S. Publ. No. 2006/0036281, which is incorporated by reference in its entirety.

Figure 8A:
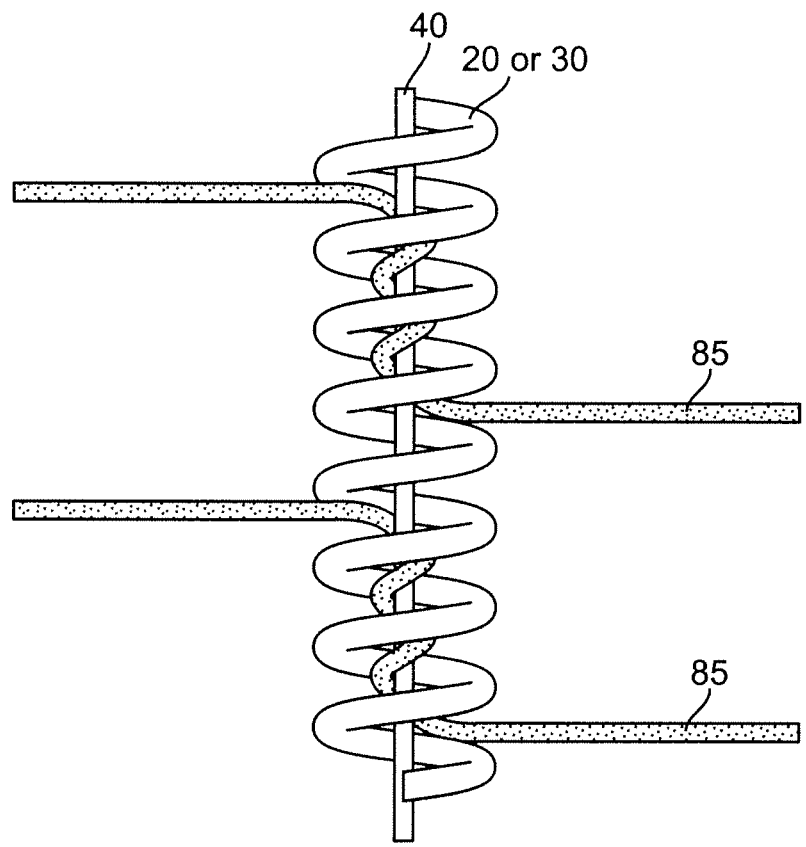
FIG. 8A illustrates one embodiment, in plan view, an exemplary wrapping pattern of the fibers around the stretch resistant member.
Figure 8B:
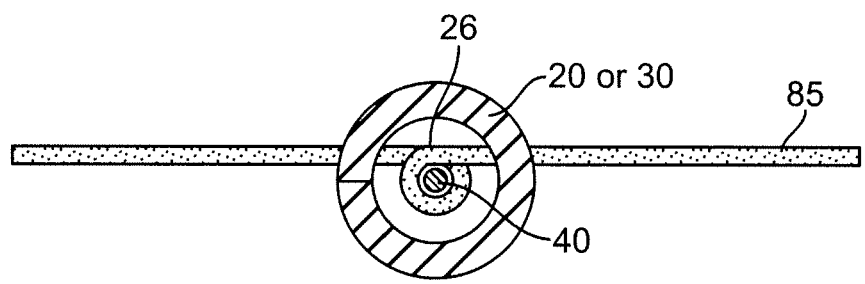
FIG. 8B is a cross-sectional view of the wrapping pattern of the fibers around the stretch-resistant member shown in FIG. 8A.

In one embodiment illustrated in FIGS. 8A and 8B, the fiber 85 is wrapped at least one or two times around the stretch-resistant member 40. In one embodiment, the fiber(s) 85 include a plurality of fibers, at least one bundle of fibers, or a plurality of fiber bundles wrapped at least one or two times round the stretch-resistant member 40.

In another embodiment, the fiber(s) 85 are enlaced through a single loop around the primary coil 20 and optionally the secondary coil 30. In another embodiment, the fiber(s) 85 are enlaced through a pair of loops of the primary coil 20 and optionally the secondary coil 30. In yet another embodiment, the fiber(s) 85 are enlaced in a "S" pattern through a plurality of loops in the primary coil 20 and optionally the secondary coil 30. In still yet another embodiment, the fiber(s) 85 are enlaced adjacent to each other in a "S" pattern on the primary coil 20 and optionally the secondary coil 30.

Materials

The primary and secondary coils 20 and 30 and rod 60 are preferably made of a biocompatible metal or metal alloy wire that does not react adversely with tissues and fluids when used in the body. The wire may be round, square, oval, triangular, or another shape. In certain embodiments the wire commonly has a diameter of from about 0.025 to about 0.09 mm, from about 0.03 to about 0.08 mm from about 0.04 to about 0.06 mm In certain specific embodiments the wire has a diameter of about 0.05 mm. In some embodiments the wire may be comprised only of a primary shape e.g., a simple single helix. In some embodiments the wire component may comprise a primary shape e.g., helical coil and a secondary shape which the coil is biased to form upon release from the catheter or guidewire. The secondary shape may comprise a complicated three dimensional shape. These shapes include spherical, cubic and other space-filling shapes, such as those created by winding the wire in a series of mobius loops. This embodiment is described in can be found in U.S. Ser. No. 12/038,737, filed on even date herewith and titled "An implant, a mandrel, and a method of forming an implant." This application is incorporated by reference in its entirety.

In other embodiments the wire can comprise a coil of coils or double helix. When it is a coil of coils, the outer or secondary diameter of the outer helix may be from about 1 to about 25 mm in some embodiments and from about 2 to 20 mm in certain other embodiments. The primary (inner) helix may typically have an outside diameter of from about 0.1 to about 0.8 mm in some embodiments, and from about 0.15 to about 0.6 mm in other embodiments and from about 0.2 to about 0.4 mm in yet other embodiments. Certain specific embodiments provide for coils having a primary diameter of about 0.28 mm sized to pass through a correspondingly dimensioned catheter. Yet other embodiments provide for coils having a primary diameter of about 0.24 mm sized to pass through a correspondingly dimensioned catheter.

In one embodiment, the material of the primary and secondary coils 20 and 30 and rod 60 are made of a material that may be heat set at a temperature of approximately 650° C. The metal or metal alloy can be radiopaque so that the position and location of the implant in the body can be monitored with radiological techniques. Suitable metals include, but are not limited to the noble metals such as the platinum group metals which include platinum, palladium, rhodium and rhenium as well as iridium, gold, silver, tungsten, and tantalum and alloys of these metals with one another. Additional metals include the super elastic metals such as "Nitinol" and the like. In one embodiment, the primary and secondary coils 20 and 30 are made of a platinum alloy, and the rod 60 is made of stainless steel.

The overall axial length of the implant 10 of this invention ranges from about 5 to about 400 mm in some embodiments and from about 10 to about 300 mm in other embodiments. This length may be selected depending upon the particular application of use and may be longer than about 400 mm in some embodiments.

The stretch-resistant member 40 and the retainer 50 are preferably made from a wide variety of materials. These materials can include any of the metals suitable for making the primary and secondary coils 20 and 30. The stretch-resistant member 40 and the retainer 50 can also be made of a radiopaque material, or of a polymer.

The stretch-resistant member 40, retainer 50, and fibers/fiber bundles 85 are preferably made of polymeric materials, and most preferably made of polypropylene. The retainer 50 is also preferably formed from a melt of the stretch-resistant member 40. The polymeric materials can include materials approved for use as implants in the body or which could be so approved. They can be nonbiodegradable polymers such as polyethylene, polyacrylics, polypropylene, polyvinylchloride, polyamides such as nylon, e.g., Nylon 6.6, polyurethanes, polyvinylpyrrolidone, polyvinyl alcohols, polyvinylacetate, cellulose acetate, polystyrene, polytetrafluoroethylene, polyesters such as polyethylene terephthalate (Dacron), silk, cotton, and the like. The nonbiodegradable materials for the polymer component can comprise polyesters, polyethers, polyamides and polyfluorocarbons.

The polymeric materials can be biodegradable as well. Representative biodegradable polymers include: polyglycolic acid/polylactic acid (PGLA), polycaprolactone (PCL), polyhydroxybutyrate valerate (PHBV), polyorthoester (POE), polyethyleneoxide/polybutylene terephthalate (PEO/PBTP), polylactic acid (PLA), polyglycolic acid (PGA), poly (p-dioxanone), poly(valerolactone), poly(tartronic acid), poly((3-malonic acid), poly(propylene fumarate), poly(anhydrides), and tyrosine-based polycarbonates. Other equivalent materials, including but not limited to stereoisomers of any of the aforementioned, may be used as well. The biodegradable polymer can be comprised of copolymers of lactic acid and glycolic acid. The copolymer can be comprised of glycolic/lactic acid in the ratio of 90:10. The ratio of glycolic to lactic acid can be chosen from 99:1; 90:10; 95:5; 50:50; 10:90; 5:95; and 1:99. The fibers can also be comprised of Nylon 6.6.

The stretch resistant member 40 and the fiber(s) 85 may also comprise a bioactive coating. The bioactive coating may be selected from growth factor, a gene, an oligonucleotide, a peptide, a marine biopolymer, a monosaccharide, a disaccharide, a polysaccharide, collagen and combinations thereof.

The illustrated stretch-resistant member 40 preferably has a tensile strength of 0.2 and 1.2 Newton. In some embodiments, the tensile strength is 0.6 Newton.

Positioning Device

The implant described herein may be delivered by a variety of suitable microcatheters and positioning devices. In one embodiment, the invention is directed to a kit having one or more implants of the invention and a positioning device. In another embodiment, the kit includes a microcatheter. Suitable microcatheters positioning devices are described in WO 2007/121405 entitled "System and Method For Mechanically Positioning Intravascular Implants" which is hereby incorporated by reference in its entirety.

In one embodiment, as illustrated in FIG. 3, the implant 10 can engage a positioning device 70 such that the ball 62 and the proximal portion of the rod 60 engage the distal end 74 of the positioning device 70. The illustrated positioning device 70 can include a positioner 75 with a positioner tube 76 having an actuator interface 77 and an implant interface 78 that terminates at an end cap 79. The end cap 79 can have a port 80 through which the rod 60 communicates with the positioner lumen 81. The positioner 75 can also include a cord 82 that occludes a portion of the port 80 to prevent the disengagement of the implant 10 from the implant interface 78.

Figure 6A:
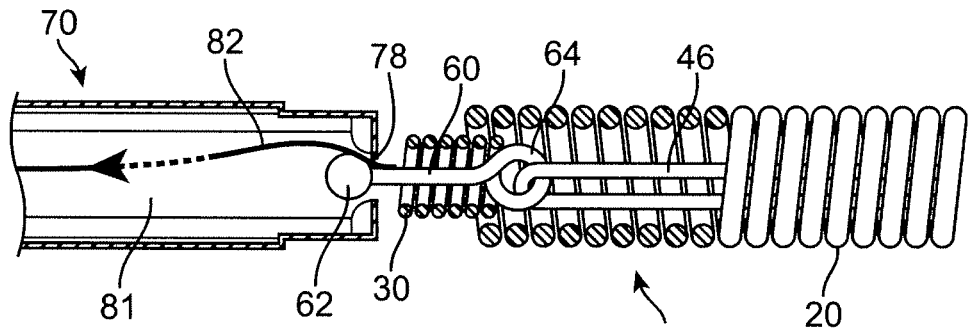
FIGS. 6A and 6B show an implant of the invention prior to detachment (FIG. 6A) and after detachment (FIG. 6B) from the positioner in partial cross-section.

It is believed that, because the stretch-resistant member 40 resists stretching, rod 60 is prevented from moving in the proximal direction out of the secondary coil 30. However, as can be seen in FIG. 6A, the stretch-resistant member 40, shown as line 46, remains sufficiently flexible to allow the rod 60 and the ball 62 to assume an angled position relative to the axis of the implant 10.

Figure 6B:
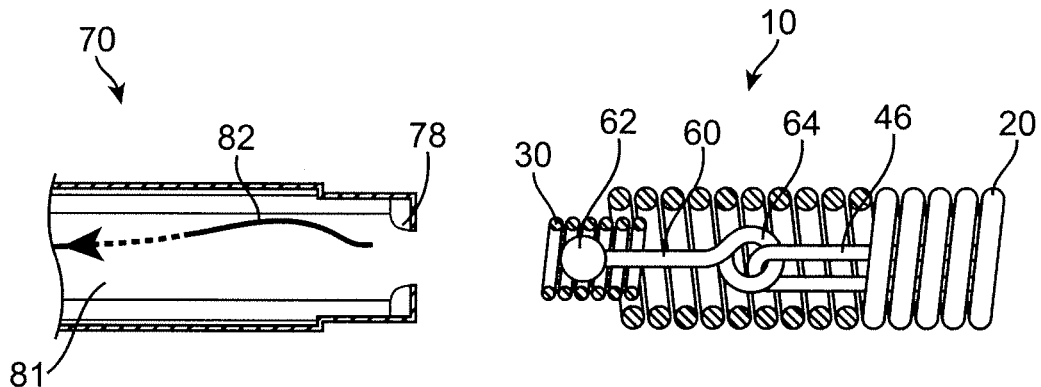

As can be seen in FIG. 6B, implant 10 can be mechanically released from positioning device 70 by retracting cord 82 so that the aperture of implant interface 78 is now sufficiently wide to permit ball 62 to traverse therethrough whereupon implant 10 is released into the vascular site. In this embodiment, ball 62 and rod 60 move in a distal direction relative to the primary coil as described below or the primary coil 20 and secondary coil 30 move proximally relative to the ball 62 and rod 60. Such movement places the ball 62 and rod 60 further into the internal lumen 26 within the primary coil 20, and in some embodiments fully enter the internal lumen 26 of the primary coil 20. In this case, ball 62 and rod 60 are fully engulfed within lumen 26 so as to form a stemless implant.

This flexibleness of the implant 10 of the invention reduces the amount of catheter kick-out. Catheter kick out refers to the movement of the catheter from its preformed shape after deployment of the implant and is typically measured by the angle of deflection, shown in FIG. 4B as 92. Implants of this invention typically have a catheter deflection of 40°, 30°, 20°, 19°, 15°, 10° or less. This reduction of catheter kick out is at least a 20%, 30%, 40%, 50%, and even 60% improvement over implants of the art.

It is also believed that, when the implant 10 is a neurological coil, the coil assumes two orientations, a microcatheter orientation when disposed in a microcatheter and a deployed orientation when external to the microcatheter. The transition of the coil from the microcatheter orientation to the deployed orientation is believed to cause the primary coil 20 to curve or bend and to extend slightly in length on at least one side of the primary coil 20, while the stretch-resistant member 40 does not so extend, thereby causing the proximal end of the implant 10 move relative to rod 60 and ball 62 and surround the rod and ball. This movement of the primary and secondary coils 20 and 30 relative to the rod 60 and ball 62, to enclose the rod and ball within the lumens of the coils 20 and 30, is believed to advantageously provide a structurally stable proximal implant end because any additional movement of the rod 60 and ball 62 is contained within the coils 20 and 30. It is further contemplated that the implant 10 is better able to conform to the desired vascular site.

Alternative Detachment Means

The implant may be deployed into the body by a number of means, including, but not limited to electrolytic detachment, chemical detachment, hydraulic detachment, thermal detachment, as well as other types of mechanical detachments. It is contemplated that the implant remains stemless after deployment into the body because after deployment, the rod 60 and ball 62 will be displaced in the inner lumen of the secondary coil 30. In other words, the ball 62 is drawn into the inner lumen of at least the secondary coil 30.

Electrolytic detachment may be performed by providing a weakened section at a junction between the implant 10 and the positioner 75. Regardless of the junction, due to the stretch-resistant member, the rod 60 and ball 62 will still be displaced in the inner lumen of the secondary coil 30 and possibly the primary coil 20. This weakened section may be easily vaporized by application an electric current. For example, the rod 60 and/or ball 62 may be replaced by a wire that may be detached by an electrical force, such as a 9V electric power source that can apply a current of about 0.3 milliamps for detachment. One example of an electrical detachment mechanism is described in U.S. Pat. No. 5,928,226, which is incorporated herein by reference.

With a chemical detachment mechanism, a dissolvable detachment section is included between the positioning device 70 and the implant 10 or at the distal end of the positioner 75. The dissolvable detachment section is dissolved, softened, swollen, degraded, or otherwise changed by the injection of a biocompatible chemical through the catheter. After the section is eroded, the rod 60 and ball 62 move distally into the lumen of the secondary coil 30 or the primary coil 20 and secondary coil 30. Some examples of chemical detachment systems include dissolvable detachment sections, such as a polymer section which is dissolved by dimethylsulfoxide, a nylon section which is dissolved by a fluorinated hydrocarbon, or sections which are dissolved by an aqueous saline solution or any of the other biocompatible solvents discussed above.

A hydraulic detachment mechanism may also be used with the implant of the invention. Hydraulic detachment means are within the scope of the art. In one embodiment, the implant interface 78 is formed of a material having a durometer such that when an appropriate fluid pressure is applied to the interior of the positioning device 70, the implant interface 78 expands thereby releasing the ball 62 and allowing the ball 62 to move distally into the lumen of the secondary coil and optionally the primary coil.

The implant of the invention may also be configured to be thermally detached from the positioner. This embodiment is similar to the electrolytic detachment described above; however, instead of applying an electric current, heat is applied thereby allowing the engagement portion to detach from the position 70 and move distally into the lumen of the catheter.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

We claim:

1. A coil implant, comprising:
   a first coil segment defining a first lumen having a first cross-sectional dimension;
   a second coil segment, having at least a portion extending within the first lumen, the second segment being connected to the first segment and defining a second lumen having a second cross-sectional dimension, less than the first cross-sectional dimension;
   a stretch-resistant member disposed within the first lumen; and
   a rod comprising a proximal portion and a distal portion, the proximal portion having a proximal cross-sectional dimension less than the second cross-sectional dimension, and being configured to extend proximally past the second segment and configured to be received within the second lumen, and the distal portion (i) coupled to the stretch-resistant member, (ii) positioned within the first lumen distal to the second segment, and (iii) having a distal cross-sectional dimension greater than the second cross-sectional dimension;

wherein the rod is capable of moving completely into the first lumen distal to the second segment.

2. The implant of claim 1, further comprising a retainer engaging a distal end of the first coil segment and coupled to the stretch-resistant member within the first lumen.

3. The implant of claim 1, wherein, within the first lumen, the rod is movable axially with respect to the first coil segment.

4. The implant of claim 1, wherein the second coil segment has an outer cross-sectional dimension less than or equal to the first cross-sectional dimension.

5. The implant of claim 1, wherein a proximal end of the first coil segment is adjacent to or partially envelopes a distal end of the second coil segment.

6. The implant of claim 1, wherein the first coil segment and the second coil segment each comprise a metal wire.

7. The implant of claim 1, wherein the first coil segment and the second coil segment comprise a primary helix that is predisposed to conform to a secondary shape when unrestrained.

8. The implant of claim 7, wherein the secondary shape is selected from helical, spheroidal, cubic, and tertiary space-filling shapes.

9. A coil implant, comprising:
a first coil segment defining a first lumen;
a second coil segment, having at least a portion extending within the first lumen, the second segment being connected to the first segment and defining a second lumen;
a stretch-resistant member disposed within the first lumen;
a rod comprising a proximal portion and a distal portion, the proximal portion being capable of moving, from a location proximal to the second segment, distally into the second lumen when released from a delivery device, and the distal portion being coupled to the stretch-resistant member in the first lumen distal to the second segment and configured to engage the second segment to limit proximal movement of the distal portion through the second lumen.

10. The implant of claim 9, wherein the first lumen has a first cross-sectional dimension; the second lumen has a second cross-sectional dimension, less than the first cross-sectional dimension; the proximal portion has a proximal cross-sectional dimension less than the second cross-sectional dimension; and the distal portion has a distal cross-sectional dimension greater than the second cross-sectional dimension.

11. The implant of claim 9, wherein the rod is capable of moving completely into the first lumen distal to the second segment.

12. The implant of claim 9, wherein, within the first lumen, the rod is movable axially with respect to the first coil segment.

13. The implant of claim 9, wherein each of the first coil segment and the second coil segment comprise a metal wire.

14. The implant of claim 9, wherein the first coil segment and the second coil segment are comprised of a primary helix that is predisposed to conform to a secondary shape when unrestrained.

15. The implant of claim 14, wherein the secondary shape is selected from helical, spheroidal, cubic, and tertiary space-filling shapes.

16. The implant of claim 9, wherein the proximal portion is capable of moving, from proximal to the second segment, distally into the second lumen when the proximal portion is disengaged from a positioner.

17. A method of treating a vascular site in a patient, comprising:
introducing an implant to the site via a positioner, the implant comprising:
a first coil segment defining a first lumen;
a second coil segment, having at least a portion extending within the first lumen, the second segment being connected to the first segment and defining a second lumen;
a stretch-resistant member disposed within the first lumen; and
a rod comprising a proximal portion and a distal portion, the proximal portion being coupled with the positioner and the distal portion being coupled to the stretch-resistant member in the first lumen distal to the second segment and configured to engage the second segment to limit proximal movement of the distal portion through the second lumen;
positioning the implant at the vascular site while the positioner is coupled with the proximal portion; and
releasing the proximal portion from the positioner, such that the proximal portion moves distally into the second lumen from a location proximal to the second segment.

18. The method of claim 17, wherein the positioner is a micro catheter.

19. The method of claim 17, wherein the releasing the implant from the positioner comprises chemical detachment, electrolytic detachment, mechanical detachment, hydraulic detachment, or thermal detachment.

20. The method of claim 17, wherein the releasing comprises moving a cord proximally to disengage the implant.

21. The method of claim 17, wherein, after the releasing, the rod is entirely contained within the first lumen and distal to the second segment.

22. The method of claim 17, wherein the implant is not stretch-resistant after the releasing.

* * * * *